United States Patent
Inaoka et al.

(10) Patent No.: US 9,976,037 B2
(45) Date of Patent: May 22, 2018

(54) COMPOSITION FOR TREATING SURFACE OF SUBSTRATE, METHOD AND DEVICE

(71) Applicant: Air Products and Chemicals, Inc., Allentown, PA (US)

(72) Inventors: Seiji Inaoka, Macungie, PA (US); William Jack Casteel, Jr., Fountain Hill, PA (US); Raymond Nicholas Vrtis, Orefield, PA (US); Kathleen Esther Theodorou, Bethlehem, PA (US); Tianniu Chen, Westford, MA (US); Mark Richard Brown, Schnecksville, PA (US)

(73) Assignee: VERSUM MATERIALS US, LLC, Tempe, AZ (US)

(*) Notice: Subject to any disclaimer, the term of this patent is extended or adjusted under 35 U.S.C. 154(b) by 87 days.

(21) Appl. No.: 15/084,169

(22) Filed: Mar. 29, 2016

(65) Prior Publication Data

US 2016/0289455 A1  Oct. 6, 2016

Related U.S. Application Data

(60) Provisional application No. 62/141,657, filed on Apr. 1, 2015.

(51) Int. Cl.
| | |
|---|---|
| *B05D 1/18* | (2006.01) |
| *C09D 4/00* | (2006.01) |
| *B08B 3/10* | (2006.01) |
| *B81C 1/00* | (2006.01) |
| *H01L 21/02* | (2006.01) |
| *C11D 11/00* | (2006.01) |
| *C11D 3/16* | (2006.01) |

(Continued)

(52) U.S. Cl.
CPC .............. *C09D 4/00* (2013.01); *B08B 3/10* (2013.01); *B81C 1/00849* (2013.01); *C11D 3/162* (2013.01); *C11D 3/36* (2013.01); *C11D 11/0047* (2013.01); *H01L 21/0206* (2013.01); *H01L 21/02041* (2013.01); *H01L 21/02068* (2013.01); *H01L 21/02129* (2013.01); *H01L 21/02282* (2013.01); *H01L 21/3105* (2013.01)

(58) Field of Classification Search
CPC ........................... B05D 1/185; C11D 11/0047
USPC ....................................... 428/472.3; 510/175
See application file for complete search history.

(56) References Cited

U.S. PATENT DOCUMENTS

| | | |
|---|---|---|
| 7,410,820 B2 | 8/2008 | Jacobs et al. |
| 2010/0219402 A1 | 9/2010 | Katsuhara et al. |
| 2012/0114974 A1* | 5/2012 | Hotchkiss ............. C07F 9/3808 428/702 |

FOREIGN PATENT DOCUMENTS

| | | |
|---|---|---|
| WO | 2008131206 A1 | 10/2008 |
| WO | 2011041358 A2 | 4/2011 |

(Continued)

OTHER PUBLICATIONS

Kellner, Kurt, et al., "Diorganosilyl-bis(O-alkylphosphonates)," Fachbereich Chemie der Martin-Luther-Universitat Halle-Wittenberg, D-06120 Halle/Saale, Germany, pp. 75-77.

(Continued)

*Primary Examiner* — Gregory Webb
(74) *Attorney, Agent, or Firm* — Anne B. Kiernan

(57) ABSTRACT

Treatment compositions and methods of treating the surface of a substrate by using the treatment composition, and a semiconductor or MEMS substrate having the treatment composition thereon.

23 Claims, 5 Drawing Sheets

(51) Int. Cl.
*C11D 3/36* (2006.01)
*H01L 21/3105* (2006.01)

(56) References Cited

FOREIGN PATENT DOCUMENTS

| WO | 2011067383 A1 | 6/2011 | | |
|---|---|---|---|---|
| WO | 2012027667 A2 | 3/2012 | | |
| WO | WO-2017053345 A1 * | 3/2017 | ........... | C09D 127/12 |

OTHER PUBLICATIONS

Lukes, Ivan, et al, "Direct Reaction of Phosphorus Acids with Hydroxy of a Silanol and on the Silica Gel Surface," J. Am. Chem. Soc. 1994, 116, 1737-1741, Dec. 31, 1994.

* cited by examiner

COMPOSITION FOR TREATING SURFACE OF SUBSTRATE, METHOD AND DEVICE

This application claims priority to the U.S. provisional application 62/141,657 filed Apr. 1, 2015 which is incorporated herein by reference in its entirety.

BACKGROUND OF THE INVENTION

The present invention relates to a treatment composition and method of treating the surface of a semiconductor or MEMS substrate and a semiconductor or MEMS substrate comprising the treatment composition thereon.

In the process of manufacturing a semiconductor device, in the lithography module, after the step of using a developer to form a pattern in a photoresist, after etching the underlying substrate and removing the photoresist, there is a pattern in the underlying metal or dielectric substrate. There is performed one or more steps of cleaning the surface of the semiconductor substrate (wafer) having the pattern thereon. Water and/or a chemical solution may be supplied to the surface of the wafer. The water may be used as a final rinse step. But after the use of the chemical solution and/or water rinse steps, there is typically performed a drying step for removing the chemical solution or water.

There is a problem that a pattern formed on the wafer may collapse due to the surface tension of the water and/or chemical solution before or during the drying step. In order to solve the problem, there is needed a new treatment composition, and method for the application of a new treatment composition.

Another problem that exists in the manufacture of semiconductor devices is caused when substrates (used in the manufacture of semiconductor devices) comprising organosilicate glass dielectric films are subjected to an etching or ashing treatment in such a way as to undesirably remove at least a portion of previously existing dielectric material and/or to change the composition of the materials that stay after the etching process near the surface that was affected by the etch process. The resulting surfaces may undesirably have hydrophilic characteristics. These treated films are often used as insulating materials in the manufacture of semiconductor devices such as integrated circuits ("ICs"), in order to ensure low dielectric constant and stable dielectric properties in these films, a way to restore a low dielectric constant would be desirable.

Additional challenges in the manufacture of MEMS or semiconductor devices, such as integrated circuits ("ICs"), involve the need for treatment compositions that can be coated on at least some area of a surface of a MEMS or semiconductor device that may comprise one or more types of materials, for examples, one or more metals and one or more insulators, etc., thereon. The treatment compositions disclosed herein may be used to change the surface characteristics of one or more areas of the exposed surfaces of the semiconductor or MEMS substrates.

BRIEF SUMMARY OF THE INVENTION

In one aspect of the invention is provided a treatment composition comprising a silane-and-phosphorus-containing compound formed by reacting a mixture comprising one or more silane-containing components and one or more phosphorus-containing components wherein at least one of the silane-containing components has the following structure:

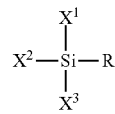

(0)

where R is selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups or halogen-substituted heteroaryl groups, ether, amine, ester, amide, and alkoxy groups, with the proviso that there is no hydrogen bonded to a nitrogen or an oxygen in said silane-containing component of structure (0); $X^1$, $X^2$ and $X^3$ are independently selected from the group consisting of halogens, alkoxy groups, organic acid groups, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester and amide groups, with the proviso that at least one of $X^1$, $X^2$ and $X^3$ is selected from the group consisting of a halogen, an alkoxy group or an organic acid group;

and at least one of said one or more phosphorus-containing components has the following structure:

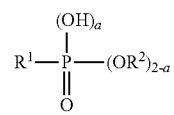

(4)

where, a is 1 or 2, and $R^1$ and $R^2$ are independently selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester, amide, and alkoxy groups; and optionally further comprising one or more non-aqueous solvents.

In another aspect of the invention is provided a treatment composition comprising silane-and-phosphorus-containing compound having the following structure:

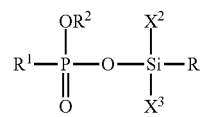

where R is selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester, amide, and alkoxy groups; $X^2$ and $X^3$ are independently selected from the group consisting of halogen, alkoxy groups, organic acid groups, hydrogens, or unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester and amide groups with the proviso that there is no hydrogen bonded to a nitrogen or an oxygen in said $X^2$, $X^3$ and R; and $R^1$ and $R^2$ are independently selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups or halogen-substituted heteroaryl groups, ether, amine, ester, amide, and alkoxy groups.

In other aspects of the invention, at least one of said $X^1$, $X^2$, or $X^3$ is a halogen; or only one of said $X^1$, $X^2$, or $X^3$ is a halogen; and further $X^1$ is a halogen and $X^2$, $X^3$, and R are independently selected from unsubstituted alkyl, aryl, and heteroaryl groups or fluorine-substituted alkyl, aryl, and heteroaryl groups; and/or said silane-containing component of structure (0) is selected from the group consisting of alkoxydimethylalkylsilane, dialkoxymethylalkylsilane, trialkoxyalkylsilane, chlorodimethylalkylsilane, dichloromethylalkylsilane, trichloroalkylsilane, alkoxydiethylalkylsilane, dialkoxyethylalkylsilane, trialkoxyalkylsilane, chlorodiethylalkylsilane, dichloroethylalkylsilane, in which the alkyl groups independently comprise 1 to 30, or 4 to 30, or 7 to 30 carbons, and wherein said carbons may have halogens substituted for some or all hydrogens attached to said carbons, and the alkoxy groups may be any $C_1$-$C_8$ alkoxy group, and may comprise halogens substituted for some or all hydrogens in the alkoxy groups.

In other aspects, the treatment composition is in accordance with any of the aspects above, and further wherein R comprises 7 to 30 carbons and/or a is 2, and $R^1$ (of structure (4)) comprises 4 to 30 carbon atoms in any of the substituted and unsubstituted alkyl, aryl and heteroaryl groups.

In other aspects of the invention alone or with other aspects, R (of structure (0)) may comprise 1 to 30, 1 to 24, or 2 to 24, or 4 to 30, 4 to 24, or 6 to 24, or 7 to 30, or 6 to 20, or 2 to 20, or 3 to 20, or 4 to 20, or 4 to 18, or 4 to 16 carbon atoms in any of the substituted and unsubstituted alkyl, aryl and heteroaryl groups described above. In other aspects alone or with other aspects $X^1$, $X^2$ and $X^3$ may independently comprise 1 to 24, or 1 to 15, or 1 to 10, or 1 to 8, or 1 to 6, or 1 to 4, or 1 to 2 carbon atoms in any of the groups described earlier for $X^1$, $X^2$ and $X^3$.

In other aspects, with any of the aspects above, the phosphorus-containing component of structure (4) is selected from the group consisting of octadecylphosphonic acid, octylphosponic acid, decylphosponic acid, dodecylphosponic acid, tetradecylphosponic acid, hexadecylphosponic acid, eicosylphosponic acid, docosylphosphonic acid and tetracosylphosphonic acid.

In other aspects of the invention, with any of the aspects above, said treatment composition may comprise one or more silane-containing components of structure (0) in excess of an amount that will react with said one or more phosphorus-containing component of structure (4) and the excess one or more silane-containing components may act as solvent for the silane-and-phosphorus-containing compound. Alternatively or additionally, said treatment composition, alone or with other aspects above may comprise one or more non-aqueous solvents selected from the group consisting of: silicone oil, 3,3',4,4'-oxydiphthalic dianhydride, benzyl alcohol, 1-octanol, NMP, glycol ether, $C_{1-40}$ aliphatic hydrocarbons; $C_{1-40}$ aromatic hydrocarbons, substituted naphthalenes, d-limonene, l-limonene, dl-limonene, orange peel oil, dipentene, halogenated hydrocarbons, fluorinated hydrocarbons, silane-containing components of structure (0), and mixtures thereof.

The treatment composition, alone or with any of the aspects above may comprise one or more non-aqueous solvents selected from the group consisting of: silane-containing components of structure (0), silicone oil, hexane, octane, decane, dodecane, tetradecane, hexadecane, octadecane, icosane, benzene, toluene, xylene, mesitylene, naphthalene, methylnaphthalene, dimethylnapthalene, trimethylnapthalene, tetramethylnapthalene, tetrahydronaphthalene, d-limonene, l-limonene, dl-limonene, orange peel oil, dipentene, methylene chloride, chloroform, 1,1,1-trichloroethane, trichloroethylene; fluorochlorohydrocarbons, fluorochlorocarbons, chlorohydrocarbons, fluorohydrocarbons, fluorocarbons, chlorocarbons, ethers of fluorochlorohydrocarbon with hydrocarbon, fluorochlorohydrocarbons, fluorochlorocarbons, chlorohydrocarbons, fluorohydrocarbons, fluorocarbons or chlorocarbons; ethers of fluorochlorocarbon with hydrocarbon, fluorochlorohydrocarbons, fluorochlorocarbons, chlorohydrocarbons, fluorohydrocarbons, fluorocarbons or chlorocarbons; ethers of chlorohydrocarbon with hydrocarbon, fluorochlorohydrocarbon, fluorochlorocarbon, chlorohydrocarbon, fluorohydrocarbon, fluorocarbon or chlorocarbons; ethers of fluorohydrocarbon with hydrocarbon, fluorochlorohydrocarbons, fluorochlorocarbons, chlorohydrocarbons, fluorohydrocarbons, fluorocarbons or chlorocarbons; ethers of fluorocarbon with hydrocarbon, fluorochlorohydrocarbon, fluorochlorocarbon, chlorohydrocarbon, fluorohydrocarbon, fluorocarbon or chlorocarbon; ethers of chlorocarbon with hydrocarbon, fluorochlorohydrocarbon, fluorochlorocarbon, chlorohydrocarbon, fluorohydrocarbon, fluorocarbon or chlorocarbon; and mixtures thereof.

In another aspect, with any of the other aspects, said one or more silane-containing components of structure (0) of the treatment composition may be selected from the group consisting of chlorotrimethylsilane, chlorodimethyloctylsilane, trichlorooctylamine, bis(triethoxysilyl)ethane, and (tridecafluoro-1,1,2,2-tetrahydrooctyl)trichlorosilane.

In another aspect, with any of the other aspects above, said treatment composition comprises: (i) 0.01 to 99.999 wt % of the one or more silane-containing components of structure (0); (ii) 0.001 to 60 wt % of the one or more phosphorus-containing components of structure (4); and (iii) 0 to 99.989 wt % non-aqueous solvent (excluding the silane-containing components of structure (0) which are included in (i)) based on the total weight of the composition; or where said treatment composition comprises: (i) 40 to 99.999 wt % of the one or more silane-containing components of structure (0); (ii) 0.001 to 10 wt % of the one or more phosphorus-containing components of structure (4); and (iii) 0 to 50 wt % non-aqueous solvent (excluding the silane-containing components of structure (0) which are included in (i)) based on the total weight of the composition; or wherein said treatment composition comprises: (i) 0.01 to 49.999 wt % of the one or more silane-containing components of structure (0); and (ii) 0.001 to 10 wt % of the one or more phosphorus-containing components of structure (4); and (iii) 50 to 99.989 wt % non-aqueous solvent (excluding the silane-containing components of structure (0) which are included in (i)) based on the total weight of the composition.

In another aspect, with any of the other aspects above, said treatment composition comprises: (i) 0 to 99.999 wt % of the one or more silane-containing components of structure (0); (ii) 0.001 to 100 wt % of the one or more silane-and-phosphorus-containing compounds; and (iii) 0 to 99.999 wt % non-aqueous solvent (excluding the silane-containing components of structure (0) which are included in (i)) based on the total weight of the composition; or where said treatment composition comprises: (i) 40 to 99.999 wt % of the one or more silane-containing components of structure (0); (ii) 0.001 to 10 wt % of the one or more silane-and-phosphorus-containing compounds; and (iii) 0 to 50 wt % non-aqueous solvent (excluding the silane-containing components of structure (0) which are included in (i)) based on the total weight of the composition; or wherein said treatment composition comprises: (i) 0.01 to 49.999 wt % of the one or more silane-containing components of structure (0); and (ii) 0.001 to 10 wt % of the one or more silane-and-phosphorus-containing compounds; and (iii) 50 to 99.989 wt % non-aqueous solvent (excluding the silane-containing components of structure (0) which are included in (i)) based on the total weight of the composition.

In another aspect, alone or with other aspects of the invention, the treatment composition comprises: (i) 0 to 99.999 wt % of the one or more silane-containing components of structure (0); (ii) 0.001 to 100 wt % of the one or more silane-and-phosphorus-containing compounds; and (iii) 0 to 99.999 wt % non-aqueous solvent (excluding the silane-containing components of structure (0) which are included in (i)) based on the total weight of the composition.

In another aspect of the invention, the silane-and-phosphorus-containing compound of the treatment composition, alone or with any other aspect of this invention, is selected from the group consisting of alkylsilyl alkylphosphonates, arylsilyl alkylphosphonates, alkylsilyl arylphosphonates, arylsilyl arylphosphonates, heteroarylsilyl alkylphosphonates, alkylsilyl heteroarylphosphonates, heteroarylsilyl heteroarylphosphonates, aryllsilyl heteroarylphosphonates and heteroarylsilyl arylphosphonates.

In another aspect, the treatment composition silane-and-phosphorus-containing compound comprises six or more carbons.

In another aspect of the invention alone or in combination with another aspect, the treatment composition comprises dimethylsilyl octadecylphosphonate.

In another aspect of the invention, along with any other aspect, the silane-and-phosphorus-containing compound of the treatment composition comprises the following structure:

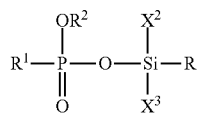

where R is selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups or halogen-substituted heteroaryl groups, or ether, amine, ester, amide, and alkoxy groups, with the proviso that there is no hydrogen bonded to a nitrogen or an oxygen; $X^2$ and $X^3$ are independently selected from the group consisting of halogen, alkoxy groups, organic acid groups, hydrogens, or any of said R, and $R^1$ and $R^2$ are independently selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl aryl and heteroaryl groups are selected from halogen-substituted straight, cyclic and branched alkyl, halogen-substituted aryl groups or halogen-substituted heteroaryl groups, or ether, amine, ester, amide, and alkoxy groups, with the proviso that there is no hydrogen bonded to a nitrogen or an oxygen.

In another aspect of the invention, alone or in combination with other aspects of the invention, the silane-and-phosphorus-containing compound of the treatment composition has the NMR shown in FIG. 6.

In another aspect of the invention, alone or in combination with other aspects of the invention, a treatment composition is provided comprising ocatanol and octadecylphosphonic acid.

In another aspect of the invention, alone or in combination with other aspects of the invention, a substrate comprising any of the treatment compositions of this invention above or otherwise disclosed herein is provided.

In another aspect of the invention, alone or in combination with other aspects of the invention, a method of treating the surface of a substrate comprising the step of contacting or coating at least a portion of the surface of the substrate with any treatment composition above or otherwise disclosed herein is provided.

In any aspect of the invention above, the treatment composition and the method of using them is for the purpose of treating, contacting or coating at least a portion of the surface of a semiconductor or MEMS substrate with the treatment composition. The substrate may be a patterned substrate.

In another aspect of the invention, alone or with other aspects is provided a method of treating the surface of a semiconductor or MEMS substrate which may be a patterned substrate comprising: optionally rinsing the (patterned) substrate by using at least an optional first pre-rinse composition in at least a first optional pre-rinse step; forming a film (which may be a hydrophobic film) on at least a portion of the surface of the (patterned) substrate by introducing a treatment composition which may also be referred to as a hydrophobic-film-forming composition onto at least a portion of the surface of the (patterned) substrate; optionally rinsing the (patterned) substrate by using at least a first optional post-rinsing composition in at least a first optional post-rinsing step; and optionally drying the (patterned) substrate, wherein said treatment (hydrophobic-film-forming) composition comprises at least one of the treatment compositions disclosed above or herein.

In an additional aspect of the invention, alone or with other aspects, the optional pre-rinse composition may comprise an optional first pre-rinse step comprising pure water and/or an optional second-pre-rinse step of water-miscible organic solvent or solvents (isopropanol, glycol ether, DMSO/NMP, etc.) and an optional third pre-rinsing step which may comprise a water-immiscible solvent or solvent mixture; and/or the optional first post-rinsing composition may be a solvent that is miscible with the above treatment or hydrophobic-film forming composition, such as, a water-immiscible organic solvent or solvent mixture, followed by an organic solvent that is water miscible in a second post-rinsing step and then water in an optional third post-rinsing step. Any of the above-described steps are optional. One or more alcohols may be used as a water-miscible solvent in any of the optional pre-rinsing steps and/or optional post-rinsing steps. In some embodiments, the optional third pre-rinsing step and the optional first post-rinsing step, just described, may be eliminated.

In an additional aspect, in combination with any other aspect, the method may comprise a substrate comprising silicon nitride and silicon oxide, $TiSi_xN_y$, $TiSi_xO_y$ and/or metals thereon.

In an additional aspect of the invention, in combination with any other aspect, the method may further comprise an ashing step to remove the hydrophobic film and/or a drying step. The drying may be accomplished by spin drying, evaporation drying, or reduced pressure drying.

DETAILED DESCRIPTION OF THE INVENTION

Figure 1:
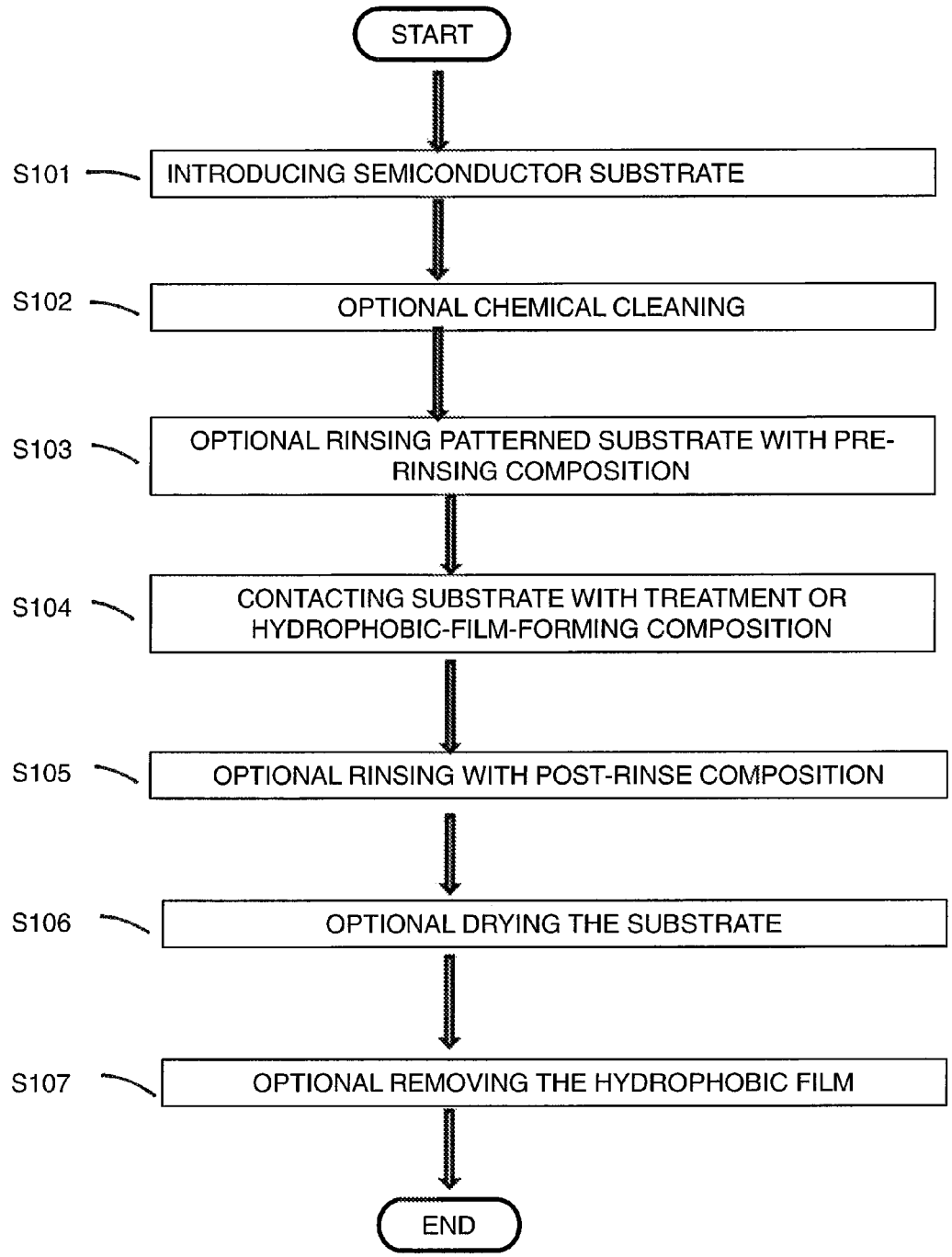
FIG. 1 is a flow chart for explaining a surface treatment method according to a first embodiment of the present invention.

The treatment composition comprises a silane-and-phosphorus-containing compound formed by reacting a mixture comprising one or more silane-containing components and one or more phosphorus-containing components and optional one or more non-aqueous solvents and other optional one or more additives. The treatment compositions are useful for treating the surfaces of Microelectromechanical systems (MEMS) or semiconductor substrates. Methods of this invention to treat MEMS or semiconductor substrates is provided.

Note, that the use of comprising and having (open terms) herein include consisting essentially of and consisting of everywhere the open terms are used as if those terms were set forth in the text. Additionally, all of the weight percents (wt %) specified herein are based on the total weight of the treatment composition unless otherwise noted.

The one or more silane-containing component is represented by the following structure (0):

In structure (0), R is selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups. Examples of substituted groups include, for example, halogen-substituted (for example, fluoro-substituted, chloro-substituted, iodo-substituted or bromo-substituted) straight, cyclic and branched alkyl or halogen-substituted (for example, fluoro-substituted, chloro-substituted, iodo-substituted or bromo-substituted) aryl groups, or halogen-substituted (for example, fluoro-substituted, chloro-substituted, iodo-substituted or bromo-substituted) heteroaryl groups. Alternative groups that can be substituted into or onto the straight, cyclic and branched alkyl, aryl or heteroaryl groups, include for examples, ether, amine, ester, amide, alkoxy, with the proviso that there is no hydrogen that is available to react with silicon, such as a hydrogen bonded to a nitrogen or oxygen. The heteroaryl groups are aryl groups comprising straight, cyclic and branched alkyl groups attached to one or more aryl groups. In some embodiments, R may comprise 1 to 30, or 1 to 24, or 2 to 24, or 4 to 30, or 4 to 24, or 6 to 24, 7 to 30, or 6 to 20, or 2 to 20, or 3 to 20, or 4 to 20, or 4 to 18, or 4 to 16 carbon atoms in any of the substituted and unsubstituted alkyl, aryl and heteroaryl groups described above.

$X^1$, $X^2$ and $X^3$ are independently selected from the group consisting of halogens, alkoxy groups, organic acid groups, hydrogen, or may be any R described above, for example, unsubstituted straight, cyclic and branched alkyl groups or unsubstituted aryl groups or unsubstituted heteroaryl groups (as described above)), or substituted straight, cyclic and branched alkyl groups or substituted aryl groups or substituted heteroaryl groups, for example, halogen-substituted (for example, fluoro-substituted, chloro-substituted, iodo-substituted, bromo-substituted) straight, cyclic and branched alkyl, aryl or heteroaryl groups (as described above), with the proviso that at least one of $X^1$, $X^2$ and $X^3$ is selected from the group comprising of a halogen, an alkoxy group or an organic acid group or a halogen-substituted (for example, fluoro-substituted, chloro-substituted, iodo-substituted, bromo-substituted) straight, cyclic and branched alkyl or aryl groups, or heteroaryl groups. In some embodiments, at least one of $X^1$, $X^2$ and $X^3$ is a halogen (for examples, fluorine, chlorine, iodine, or bromine), more preferably only one of $X^1$, $X^2$ and $X^3$ is a halogen. $X^1$, $X^2$ and $X^3$ may independently comprise 1 to 24, or 1 to 15, or 1 to 10, or 1 to 8, or 1 to 6, or 1 to 4, or 1 to 2 carbon atoms in any of the substituted and unsubstituted alkyl, aryl and heteroaryl groups described above. In some embodiments, $X^1$ is a halogen (for example, fluorine, chlorine, bromine or iodine) and $X^2$ and $X^3$ independently comprise any of the substituted and unsubstituted alkyl, aryl and heteroaryl groups described above having 1 to 8, or 1 to 6, or 1 to 4, or 1 to 2 carbon atoms. Alternatively, $X^1$ is a halogen (for example, fluorine, chlorine, bromine or iodine) and $X^2$ and $X^3$ independently comprise an unsubstituted alkyl, aryl and heteroaryl (as described above) groups having 1 to 10, or 1 to 8, or 1 to 6, or 1 to 4, or 1 to 2 carbon atoms. Alternatively, $X^1$ is a halogen (for example, fluorine, chlorine, bromine or iodine) and $X^2$ and $X^3$ independently comprise unsubstituted alkyl groups having 1 to 10, or 1 to 8, or 1 to 6, or 1 to 4, or 1 to 2 carbon atoms. $X^1$ may be chlorine.

In some embodiments, R can be an alkyl or substituted alkyl group, while each of $X^1$, $X^2$ and $X^3$ can independently be halogen such as fluorine or chlorine, an unsubstituted alkyl group, a substituted alkyl group, for examples, halogen-substituted alkyl groups, alkoxy groups (for examples, methoxy, ethoxy or propoxy or any 4 to 20 carbon containing alkoxy groups), or organic acid groups, such as acetoxy groups or propionic groups. Typically, the unsubstituted or substituted alkyl groups (for example, alkoxy groups) are 4 to 20 carbons or 6 to 18 carbons. The substituted or unsubstituted alkyl groups may be straight chains, branched or cyclic and may have 1 to 20 carbons, or 4 to 18 carbons. Examples of the halogen substituted alkyl groups, where the hydrogens of the alkyl group are partially or fully replaced with a halogen and the halogen is fluorine (F), may be described as $C_xF_{(2x+1-y)}H_y-$, where x is from 1 to 24 and y is from 0 to x/2, or x is from 4 to 18 and y is from 0 to x/2, x is from 6 to 18 and y is from 0 to x/2. For other halogens F may be replaced with Cl, Br, or I in the same formula. For some silane-containing components useful in the treatment composition of this invention, 2 of $X^1$, $X^2$ and $X^3$ in structure (0) are halogen- (e.g. fluorine- or chlorine-) substituted alkyl groups and the $3^{rd}$ of $X^1$, $X^2$ and $X^3$ in structure (0) is a halogen (e.g. fluorine or chlorine) and in still other silane-containing components one of $X^1$, $X^2$ and $X^3$ in structure (0) is a halogen (e.g. fluorine or chlorine) and the other two of $X^1$, $X^2$ and $X^3$ and R are unsubstituted or substituted alkyl groups.

Examples of suitable silane-containing components of structure (0) useful in the treatment composition include alkoxydimethylalkylsilane, dialkoxymethylalkylsilane, trialkoxyalkylsilane, chlorodimethylalkylsilane, dichloromethylalkylsilane, trichloroalkylsilane, alkoxydiethylalkylsilane, dialkoxyethylalkylsilane, trialkoxyalkylsilane, chlorodiethylalkylsilane, dichloroethylalkylsilane, (in which the alkyl groups are typically 1 to 24, or 2 to 24, or 3 to 20, or 4 to 20, or 4 to 24, or 6 to 20, or 4 to 18 carbons, in which fluorine, chlorine, iodine and bromine atoms, preferably fluorine, can substitute part or all of hydrogen atoms attached to carbon atoms in the alkyl groups) and the like. And the alkoxy groups may be methoxy, ethoxy, propoxy, butoxy or $C_1$-$C_8$ alkoxy groups, and may comprise halogens substituted for some or all of the hydrogen atoms, for example, fluorine atoms, attached to carbon atoms in the alkoxy groups. Examples of structure (0) include: trimethylsilyl acetate, trimethylsilyl propionate, trimethylsilyl butyrate and trimethylsilyloxy-3-penten-2-one.

Additional examples of silane-containing components of structure (0) include: chlorotrimethylsilane, chlorodimethyloctylsilane, trichlorooctylamine, bis(triethoxysilyl)ethane, and (tridecafluoro-1,1,2,2-tetrahydrooctyl)trichlorosilane.

The treatment composition comprising a silane-and-phosphorus-containing compound is formed by reacting a mixture comprising one or more silane-containing components of structure (0) and one or more phosphorus-containing components having the following structure:

where, a is 1 or 2, and $R^1$ and $R^2$ (if a is 1) are independently selected from hydrogen, unsubstituted straight, cyclic and branched alkyl groups, unsubstituted aryl groups, unsubstituted heteroaryl, substituted straight, cyclic and branched alkyl groups, substituted aryl groups, or substituted heteroaryl groups. Examples of substituted groups include, for example, halogen-substituted (for example, fluoro-substituted, chloro-substituted, iodo-substituted or bromo-substituted) straight, cyclic and branched alkyl or halogen-substituted (for example, fluoro-substituted, chloro-substituted, iodo-substituted or bromo-substituted) aryl groups, or halogen-substituted (for example, fluoro-substituted, chloro-substituted, iodo-substituted or bromo-substituted) heteroaryl groups. Alternative groups that can be substituted into or onto the straight, cyclic and branched alkyl or aryl groups, include for examples, ether, amine, ester, amide, alkoxy, with the proviso that there is no hydrogen that is available to react with silicon, that is, that there is no hydrogen bonded to a nitrogen or oxygen. In some embodiments, $R^1$ and/or $R^2$ may independently comprise 1 to 30, or 1 to 24, or 1 to 20 or 1 to 18, or 2 to 24, or 4 to 30, or 4 to 24, or 4 to 22, or 6 to 24, or 6 to 20, or 6 to 30, 8 to 30, 8 to 24, or 10 to 30, or 10 to 20, or 2 to 20, or 10 to 24, or 3 to 20, or 4 to 20, or 4 to 18, or 4 to 18 carbon atoms in any of the substituted and unsubstituted alkyl, aryl and heteroaryl groups described above.

The phosphorus-containing component may be a phosphonic acid. In one embodiment, a is 2. In another embodiment a is 2 and $R^1$ is an unsubstituted alkyl group having 1 to 24, or 1 to 20, or 4 to 20, 4 to 18, or 8 to 24, or 10 to 20, or 1 to 18 carbons.

Examples of phosphonic acids useful in this invention include octadecylphosphonic acid, octylphosonic acid, decylphosponic acid, dodecylphosponic acid, tetradecylphosponic acid, hexadecylphosponic acid, eicosylphosponic acid, docosylphosphonic acid and tetracosylphosphonic acid.

In the embodiment in which a phosphorus-containing component and a silane containing component are used in the treatment or hydrophobic-film-forming composition, the treatment or hydrophobic-film-forming composition may hydrophobilize oxide-containing surfaces (TEOS, thermal oxide, $TiSi_xO_y$, low-k film) as well as nitride-containing surfaces (titanium nitride, $TiSi_xN_y$, silicon nitride). The silane-containing component, such as organosilanes, tends to hydrophobilize the oxide surface, and the phosphonic acid, such as, octadecylphosphonic acid (ODPA) may hydrophobilize the nitride surface.

In addition to the one or more silane-and-phosphorus-containing components, the treatment or hydrophobic-film-forming composition may further comprise a organic or inorganic, preferably, non-aqueous solvent. The solvent, if present may be any non-aqueous solvent useful with the silane-and-phosphorus-containing component and/or the silane-containing component. The silane-containing component(s) of structure (0) used to make the treatment composition may be in the form of a liquid and may act as a solvent for the phosphorus-containing component and/or the silane-and-phosphorus-containing compound of the treatment composition, especially when the silane containing component(s) is(are) present in excess amounts. (Excess amounts means in amounts in excess of the molar amount of silane-containing component that will react with the molar quantity of the phosphorus-containing component to form the silane-and-phosphorus-containing-compound in the treatment composition of this invention. In some embodiments the reaction will take place in equimolar amounts.) In alternate embodiments, in addition to the excess of one or more silane-containing components of structure (0), or in the alternative to the excess of one or more silane-containing components of structure (0), the combination of the phosphorus-containing component and the silane-containing component, and/or the silane-and-phosphorus-containing compound in a uniform solution may optionally include the addition of an organic or inorganic solvent or mixtures thereof.

Useful organic solvents in the treatment composition may include 3,3',4,4'-oxydiphthalic dianhydride, benzyl alcohol, isopropyl alcohol, 1-octanol, N-Methyl-2-pyrrolidone (NMP) and glycol ether that shows good solubility of the phosphorus-containing component, for example, the phosphonic acid. (The discovery that some of those solvents had good solubility relative to known solvents for the phosphorus-containing component is one of the inventions.) However, it was discovered that the silane-and-phosphorus-containing compound is soluble in many more solvents and at much greater amounts than the phosphorus-containing component alone. Solvents that can be used in the treatment or hydrophobic-film-forming composition may include: $C_{1-40}$ aliphatic hydrocarbons including hexane, octane, decane, dodecane, tetradecane, hexadecane, octadecane, icosane, and mixtures of any of these solvents; $C_{1-40}$ aromatic hydrocarbons including benzene, toluene, xylene mesitylene, naphthalene, substituted naphthalenes, tetrahydronaphthalene, methylnaphthalene, dimethylnapthalene, trimethylnaphthalene, tetramethyl napthalene, and mixture of any of any of these; other non-polar hydrocarbon solvents including d-limonene, l-limonene, dl-limonene, orange peel oil, dipentene, silicone oils (for examples, polydimethylsiloxanes (PDMS)); halogenated hydrocarbons, including methylene chloride, chloroform, 1,1,1-trichloroethane, trichloroethylene; fluorinated solvents including a variety of fluorinated hydrocarbons, such as, fluorochlorohydrocarbons, fluorochlorocarbons, chlorohydrocarbons, fluorohydrocarbons, fluorocarbons, chlorocarbons, ethers of fluorochlorohydrocarbon with hydrocarbon, fluorochlorohydrocarbons, fluorochlorocarbons, chlorohydrocarbons, fluorohydrocarbons, fluorocarbons or chlorocarbons; ethers of fluorochlorocarbon with hydrocarbon, fluorochlorohydrocarbons, fluorochlorocarbons, chlorohydrocarbons, fluorohydrocarbons, fluorocarbons or chlorocarbons; ethers of chlorohydrocarbon with hydrocarbon, fluorochlorohydrocarbon, fluorochlorocarbon, chlorohydrocarbon, fluorohydrocarbon, fluorocarbon or chlorocarbons; ethers of fluorohydrocarbon with hydrocarbon, fluorochlorohydrocarbons, fluorochlorocarbons, chlorohydrocarbons, fluorohydrocarbons, fluorocarbons or chlorocarbons; ethers of fluorocarbon with hydrocarbon, fluorochlorohydrocarbon, fluorochlorocarbon, chlorohydrocarbon, fluorohydrocarbon, fluorocarbon or chlorocarbon; ethers of chlorocarbon with hydrocarbon, fluorochlorohydrocarbon, fluorochlorocarbon, chlorohydrocarbon, fluorohydrocarbon, fluorocarbon or chlorocarbon and mixtures of those and/or any of the solvents listed above. In some embodiments, the solvents are d-limonene, silicone oil, toluene, methylene chloride, tetrahydronaphthalene, or mixtures thereof.

The content of the one or more silane-containing components of structure (0) added to the treatment or hydrophobic-film-forming composition may be any amount, for examples, 0.001 to 99.999%, or 0.01 to 99.99%, or 0.1 to 99.9%, or 0.01 to 70%, or 0.01 to 60%, or 0.001 to 50%, or 0.001 to 30%, or 0.001 to 20% based on the total weight of the treatment composition. Alternatively, the one or more silane-containing components of structure (0) may be added to the treatment composition in amounts from 20 to 99.999%, or 30 to 99.999%, or 40 to 99.999%, or 50 to 99.999%, or 60 to 99.999%, or 70 to 99.999%, or 80 to 99.999% based on the total weight of the treatment composition. The weight percents specified in this paragraph include many of the embodiments that have the one or more silane-containing components of structure (0) in excess of the amount that will react with the phosphorus-containing components of structure (4) to form the silane-and-phosphorus containing compounds in the treatment compositions.

The content of the one or more phosphorus-containing components of structure (4) added to the treatment or hydrophobic-film-forming composition may be any amount, for examples, 0.001 to 90%, or 0.001 to 80%, or 0.001 to 70%, or 0.001 to 60%, or 0.001 to 50%, or 0.001 to 40%, or 0.001 to 30%, or 0.001 to 20%, or 0.001 to 10% based on the total weight of the composition.

When the non-aqueous solvent is present, it may be used in any amount. For examples, the solvent may be used from 0 to 99.989 wt %, or 0.01 to 99.989 wt %, or 0.01 to 99.989 wt %, or 10 to 99.989 wt %, or 20 to 99.989 wt %, or 30 to 99.989 wt %, or 40 to 99.989 wt %, or 50 to 99.989 wt %, or 0 to 60 wt %, or 0 to 50 wt %, or 0.1 to 40 wt %, or 0.1 to 30 wt %, or 0.1 to 20 wt %, or 0.1 to 10 wt %. The content of the phosphonic-containing component and the silane-containing component in the hydrophobic-film-forming or treatment composition is preferably from 0.001 to 100 wt %, or 0.002 to 100 wt %, or 0.011 to 100 wt %, or 0.001 to 50 wt %, or 50 wt % to 100%, or 0.001 to 10 wt %, or 0.001 to 20 wt %.

In some embodiments the treatment composition comprises: (i) 0 to 99.999 wt % of the one or more silane-containing components of structure (0); (ii) 0.001 to 100 wt % of the one or more silane-and-phosphorus-containing compounds; and (iii) 0 to 99.999 wt % non-aqueous solvent (excluding the silane-containing components of structure (0) which are included in (i)) based on the total weight of the composition; or (i) 40 to 99.999 wt % of the one or more silane-containing components of structure (0); (ii) 0.001 to 60 wt % of the one or more silane-and-phosphorus-containing compounds; and (iii) 0 to 50 wt % non-aqueous solvent (excluding the silane-containing components of structure (0) which are included in (i)) based on the total weight of the composition; or (i) 0 to 49.999 wt % of the one or more silane-containing components of structure (0); and (ii) 0.001 to 50 wt % of the one or more silane-and-phosphorus-containing compounds; and (iii) 50 to 99.989 wt % non-aqueous solvent (excluding the silane-containing components of structure (0) which are included in (i)) based on the total weight of the composition.

To make the treatment compositions of this invention, the components are combined and stirred and optionally heated.

In one embodiment the phosphonic-containing component and the silane-containing component react to form a phosphonic-and-silane-containing compound. In one embodiment, the following reaction may take place:

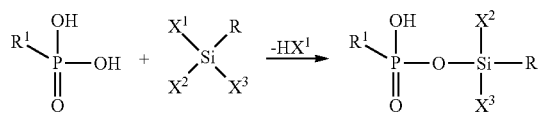

with R, $R^1$, $X^1$, $X^2$, and $X^3$ being selected from the groups described above as if it were all repeated here. In many embodiments, the reaction between the silane-containing component and the phosphorus-containing component occurs at room temperature upon the combination of the silane-containing component and phosphorus-containing components in a container with or without the addition of a solvent. Optionally, the composition may be heated up to 100° C., typically 80° C. and/or stirred for at least a few minutes. In some embodiments the reaction may take longer; the completion of which may be confirmed by NMR. The reaction to form the silane-and-phosphorus-containing compound may occur before, during and/or after the addition of solvent or other additives to the treatment composition. In one embodiment, the silane-and-phosphorus-containing compound (reaction product) is an alkylsilyl alkylphosphonate. The silane-and-phosphorus-containing compound (reaction product) typically has higher solubility in solvent as compared to the phosphorus-containing component prior to the reaction, and typically makes it possible to dissolve higher amounts of the phosphorus-containing component as part of the treatment composition of this invention than the phosphorus-containing component alone in solvent. The solubility of the phosphorus-containing component alone in known solvents was no more than approximately 0.01 wt % at room temperature. In the treatment composition of this invention, the silane-and-phosphorus-containing compound has increased the solubility of the phosphorus-containing component, in some cases approximately 2 times or more, or approximately 3 times or more, or 4 times or more, or 5 times or more as compared to the solubility of the unreacted phosphorus-containing component in the same solvent.

If desired, the silane-and-phosphorus-containing compound can be separated from the reaction mixture and used in a neat composition and/or it can be dissolved in a solvent or a mixture of solvents to make the treatment compositions of this invention. Note, a neat composition can be used as a treatment composition of this invention, when a liquid at room temperature is required, when one or both of the silane-containing component and the phosphorus-containing component have low enough molecular weights that the silane-and-phosphorus-containing compound is a liquid at room temperature or when an excess of the silane-containing component is used and it is a liquid at room temperature and acts as a solvent for the silane-and-phosphorus-containing compound. One solvent or solvent mixture, or no solvent, can be used to combine the silane-containing-component and the phosphorus-containing-component (and the silane-and-phosphorus-containing-compound), and an alternate solvent or solvent mixture can be substituted for the original solvent or solvent mixture, or added to the silane-and-phosphorus-containing-compound to form the treatment composition as desired for the substrate to be treated.

Alternatively, in other embodiments, as discussed above a molar excess of the silane-containing component can be added relative to the phosphorus-containing component present with or without other non-aqueous solvent present. The reaction will consume all of the phosphorus-containing component to make the silane-and-phosphorus-containing compound and the excess silane-containing component may remain in the treatment composition. Solvent may be added thereto if desired.

Additional additives can be used in the treatment or hydrophobic-film-forming composition, for examples, polyvinylpyrrolidone (PVP), hydrochloric acid (35%) and acetic acid. The additives can be present in an amount between from 0.01 to 20 wt %, or 0.5 to 10 wt %, or 0.1 to 1.0 wt % based on the total weight of the composition.

In addition to the silane-containing components of structure (0), other silane-containing components of the following structures (1) and (2) and others may be used in combination with the phosphorus-containing component and the optional solvent.

In the structure (1), $R^1$ represents a hydrogen atom, or a saturated or unsaturated alkyl group with 1 to 20 carbon atoms; $R^2$ represents a saturated or unsaturated alkyl group with 1 to 20 carbon atoms, a saturated or unsaturated cycloalkyl group with 1 to 20 carbon atoms, or a saturated or unsaturated heterocycloalkyl group with 1 to 20 carbon atoms; and $R^1$ and $R^2$ may link to each other to form a saturated or unsaturated heterocycloalkyl group having a nitrogen atom with 1 to 20 carbon atoms. A specific example of silane-containing components of structure (1) includes: tetramethyl silyl dimethylamine (TMSDMA).

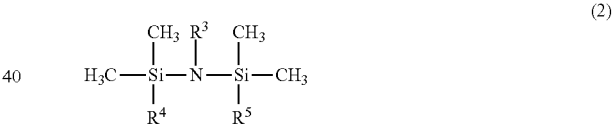

In the structure (2), $R^3$ represents a hydrogen atom, a methyl group, a trimethylsilyl group, or a dimethylsilyl group; and $R^4$ and $R^5$ each independently represent a hydrogen atom, a methyl group, an alkyl group, or a vinyl group. Specific examples of silane-containing components of structure (2) include: hexamethyldisilazane (HMDS), and trimethylsilyl diethylamine (TMSDEA).

Examples of the silane-containing component represented by the above structure (1) include N,N-dimethylaminotrimethylsilane, N,N-diethylaminotrimethylsilane, t-butylaminotrimethylsilane, allylaminotrimethylsilane, trimethylsilylacetamide, trimethylsilylpiperidine, trimethylsilylimidazole, trimethylsilylmorpholine, 3-trimethylsilyl-2-oxazolidinone, trimethylsilylpyrazole, trimethylsilylpyrrolidine, 2-trimethylsilyl-1,2,3-triazole, 1-trimethylsilyl-1,2,4-triazole, and the like.

Further, examples of the silane-containing component represented by the above structure (2) include hexamethyldisilazane, N-methylhexamethyldisilazane, 1,2-di-N-octyltetramethyldisilazane, 1,2-divinyltetramethyldisilazane, heptamethyldisilazane, nonamethyltrisilazane, tris(dimethylsilyl)amine, and the like.

Of these, N,N-dimethylaminotrimethylsilane (DMATMS) may be used in the treatment composition.

It is possible to use, the silane-containing components of structure (1) and (2) and others in the treatment composition of this invention including for example any of the following: Hexamethyldisilazane (HMDS), tetramethyl silyl dimethylamine (TMSDMA), tetramethyl silyl diethylamine (TMSDEA), Tetraethyl orthosilicate (TEOS), dimethylsilyldiethylamine (DMADEA), dimethylsilyldimethylamine (DMSDMA), tetramethyldisilazane (TMDS), bis(dimethylamino)dimethylsilane (BDMADMS), bis(dimethylamino) methylsilane (BAMS), and mixtures thereof.

If the other silicone-containing components of structure (1), and (2) or others are present in the treatment composition, they should be used in any amount as long as the silane-and-phosphorus-containing compound is present.

In one embodiment, one silane-containing component of structure (0) is used in the treatment or hydrophobic-film-forming composition. In another embodiment, two or more silane-containing components are employed in the hydrophobic-film-forming composition. In yet another embodiment, three or more silane-containing components are employed in the hydrophobic-film-forming composition. Of the embodiments having more than one silane-containing component therein, they may all be of structure (0) or a mix of components of structure (0) with components of structure (1) and/or components of structure (2) and/or others in any combination.

The invention also includes the method of using the treatment composition described above for surface modification, for examples, to increase hydrophobicity or to modify the surface energy, or for low k restoration.

A method of treating the surface of a substrate with the treatment composition, according to a first embodiment of the present invention, will be described with reference to a flow chart shown in FIG. 1 and a sectional view of a main part of a surface treatment apparatus shown in FIG. 2. The surface treatment apparatus shown in FIG. 2 is a batch type apparatus configured to collectively perform cleaning and drying of a plurality of substrates.

Although the embodiments of the methods of the invention described in conjunction with the figures described below may be described as being useful for "patterned substrates", it is understood that any "semiconductor or MEMS substrate" or "substrate" meaning any semiconductor substrate or MEMS substrate that is blank, patterned, structured, unstructured, having bumps, or no materials thereon, or others may be used in the methods of this invention to at least partially coat the substrates with a treatment composition of this invention. Further, it is understood that although the specific embodiments described below may refer to patterned substrates in the lithography and etching modules, any semiconductor or MEMS substrates at any point of the process of manufacturing the semiconductor or MEMS substrates, may be substituted for the patterned substrates and treated with the treatment compositions of this invention. Additionally, although the substrate is referred to as comprising a silicon base, any known or future substrates, including compound semiconductor substrates, such as II-VI (Zn—Se, Cd—Te) and III-V (Ga—N, Ga—As) can be substituted for it. And although the purpose of coating the patterned substrates described below is primarily to prevent pattern collapse, the methods described below using patterned or other substrates could be primarily for the other benefits of the invention described elsewhere herein.

The semiconductor wafer having a pattern thereon will be referred to as a "patterned substrate" or a "patterned semiconductor substrate". The substrate or patterned substrate is typically a semiconductor wafer having one or more layers on a silicon wafer base. The layers thereon, if present, have been deposited by multiple lithography, etch, deposition, planarization and other steps that are used to deposit layers on a semiconductor wafer. The layers on any substrate or patterned substrate may comprise organic or inorganic materials—typically metals (like Al, Cu, Co, Ti, etc.), hard mask material (TiN, TaN, etc.), dielectrics (siloxane-containing material including silicon oxide, thermal oxides, TEOS, low-k dielectrics, Air Products' DEMS C8 or DEMS ATRP) as well as organic or polymer materials (like spin-on low-k dielectrics, as well as patterned photoresist layer). (However, again, in other embodiments of the invention, the semiconductor or MEMS substrate may comprise any materials thereon at any point in the process of making an integrated circuit or MEMS device as discussed above. Alternative substrates can therefore be substituted for the patterned substrates in the following description. The method of this invention may be used to modify surfaces to change the wetting characteristics, and/or to prevent pattern collapse of patterns, and/or to modify the surface energy which can be used to improve or decrease the adhesion between surfaces.)

Figure 2:
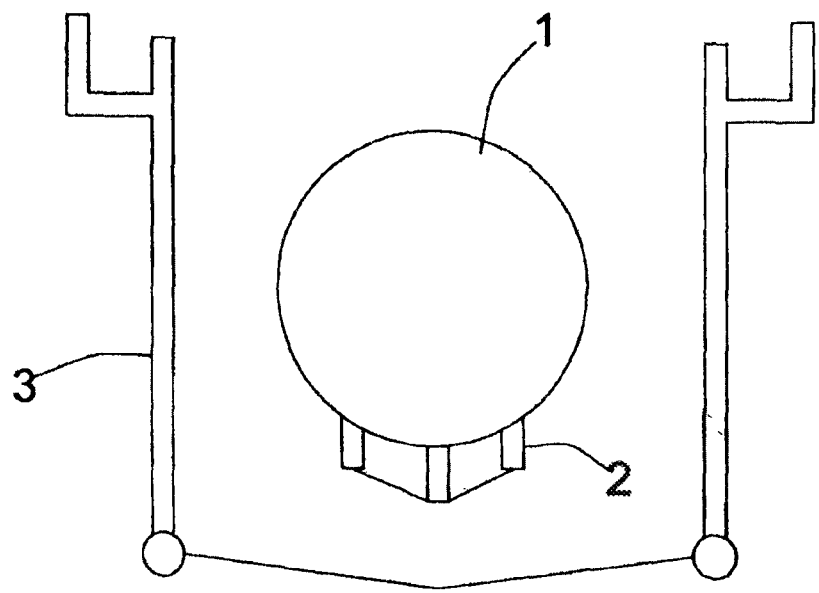
FIG. 2 is a figure showing a schematic configuration of a surface treatment apparatus according to the first embodiment.

Step S101 in FIG. 1, involves introducing a patterned substrate (wafer) 1 after development of the pattern using a developer into a treatment tank 3, followed by etch of layer underneath photoresist and removal of photoresist after the etch process. (The steps described herein may occur before or after the etching step or in alternative embodiments, there is no etch step prior to coating the substrate with the treatment composition of the invention). As shown in FIG. 2, the substrate may be held by a substrate holding section 2 while being introduced.

Optional Step S102 involves an optional cleaning of the patterned by contacting the substrate with a chemical solution. The chemical solution may be supplied from a cleaning chemical solution supplying section (not shown) to the treatment tank 3. The chemical solution may be any type of plasma, gaseous or liquid compositions designed for cleaning of the (patterned) substrate before or after the etching process.

Optional Step S103 involves rinsing the (patterned) substrate 1 with a pre-rinse solution which may be water (deionized water (DI) or otherwise purified water) and may be supplied from the treatment chemical solution supplying section to the treatment tank 3, so that components of the chemical solution used in step S102 are removed from the wafer and the treatment tank. Alternatively, the optional pre-rinse solution may be an organic solvent that is miscible with the treatment composition (or hydrophobic film forming solution) applied in Step 104. The organic solvent may be used alone in a first pre-rinse step, or in an alternate embodiment, an organic solvent pre-rinse step (may be a second and/or third pre-rise step) may be subsequent to the water pre-rinse step (which may be a first pre-rinse step). Examples of such solvents include organic solvents such as water miscible solvents, such as alcohols, tetrahydrofuran, IPA, THF, ethanol, methanol, butanol, acetone, DMSO, NMP, glycol ether. Alternatively, the pre-rinse solution may be selected from aprotic organic solvents such as toluene, methylene chloride, xylenes, octane, decane, dodecane, octadecane, d-limonene, naphthalene, substituted naphthalene, tetrahydronaphthalene, dimethylsiloxane or any solvent that is listed herein as useful in the treatment composition (which may be used in a single pre-rinse step or in combination with the first pre-rinse and/or second pre-rinse steps). In one embodiment, the first pre-rinse composition may comprise water; the second pre-rinse composition may comprise a water-miscible solvent and the third pre-rinse composition may comprise an aprotic organic solvent or any solvent described herein as useful in the treatment composition.

Figure 3:
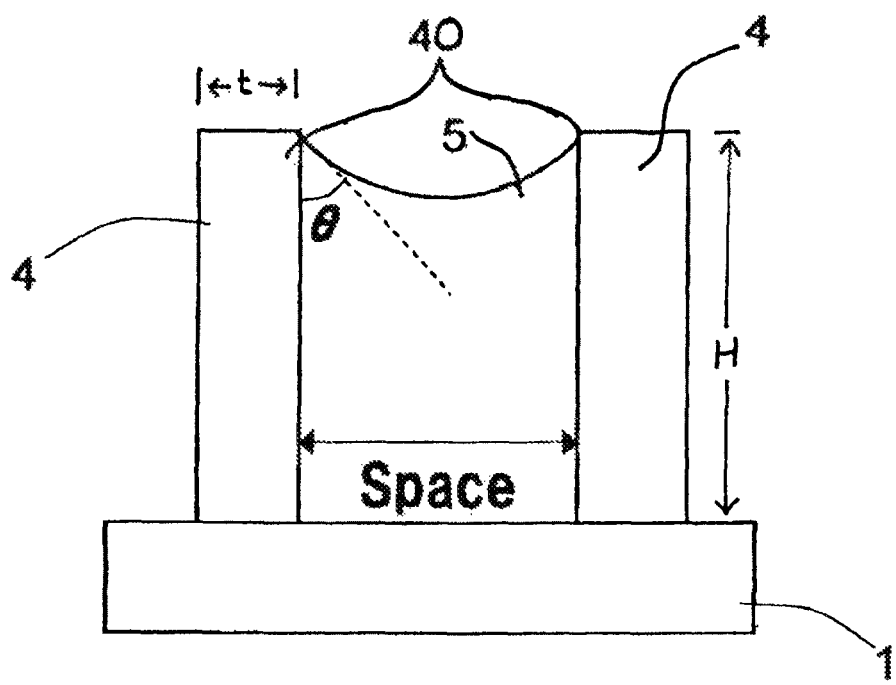
FIG. 3 is a figure for explaining surface tension of a solution, which is applied to a pattern on a semiconductor or MEMS substrate.

Step S104 involves forming film on the surfaces 1 or 4 or both 1 and 4 of FIG. 3 of the (patterned) substrate by contacting the substrate with a treatment composition (hydrophobic-film-forming composition) on all or a portion of the substrate. The treatment or hydrophobic-film-forming composition may be supplied to the treatment tank 3 from the chemical solution supplying section. In some embodiments there is no water, nor aqueous-containing solution, even in residual amounts, present on the surface of the substrate just prior to or during the step of forming the protective film on the surface of the substrate. In those embodiments any solvent, if any, present on the substrate prior to the introduction of the treatment composition will comprise a non-aqueous, organic solvent. In some embodiments, the first pre-rinse step may involve contacting the substrate with water, followed by a second pre-rinse step which involves contacting the substrate with alcohols, tetrahydrofuran, IPA, THF, ethanol, methanol, butanol, acetone, DMSO, NMP, glycol ether, and a third pre-rinsing step which involves contacting the substrate with an organic solvent, such as toluene, methylene chloride, xylenes, octane, decane, dodecane, octadecane, d-limonene, naphthalene, substituted naphthalene, tetrahydronaphthalene, dimethylsiloxane or any solvent useful in the treatment composition.

Optional Step S105 involves rinsing any excess treatment composition (hydrophobic-film-forming composition) off the substrate by contacting the substrate with a post-rinsing solution (also referred to as a post-rinse solution herein) that may be supplied to the treatment tank 3 from the treatment chemical solution supplying section. The optional post-rinse step may comprise more than one application of the rinse solution or solutions. The optional post-rinse solution(s) may be the same solution as any of the optional pre-rinse solution(s) or it may be a different composition and it is preferably miscible with both the treatment composition (hydrophobic film forming composition) and any additional optional post-rinse solution(s). In one embodiment, the post-rinse method steps may comprise a first post-rinse step which involves contacting the substrate with an organic solvent, for examples, toluene, methylene chloride, xylenes, octane, decane, dodecane, octadecane, d-limonene, naphthalene, substituted naphthalene, tetrahydronaphthalene, dimethylsiloxane, or the like or mixtures thereof, followed by a second pre-rinse step, which may involve contacting the substrate with water miscible solvents such as, alcohols, tetrahydrofuran, IPA, THF, ethanol, methanol, butanol, acetone, DMSO, NMP, glycol ether or the like and mixtures thereof, and a third pre-rinsing step which may be water.

Optional Step S106 involves drying the (patterned) substrate 1. For example, the (patterned) substrate 1 may be pulled up from the treatment tank 3, and is thereafter subjected to evaporation drying by supplying dry air from a gas supplying section (not shown). Alternatively or additionally, an optional reduced pressure drying method may be used.

Further, the optional drying step may also be performed in such a manner that a drying composition is supplied to the upper space of the treatment tank 3 from a drying chemical supplying section (not shown) in the form of liquid, vapor, or mist and in a non-mixed state or in a state mixed with a gas such as nitrogen, and that the level of the post-rinse solution that may be water in which the (patterned) substrate 1 is immersed is gradually lowered by draining the post-rinse solution. Further, the drying composition may be alcohol such as IPA or the like or a solution with low surface tension, such as hydrofluoroether (HFE).

Since a pattern formed on the (patterned) substrate 1 is covered with the treatment composition which may form a hydrophobic film, the contact angle θ of solution may be made to become large (close to 90°). In alternative embodiments, the angle θ may be from 80-120°. The larger contact angles may be achieved by increasing the amount of the treatment composition introduced (coated) onto the surface, or by repeating the forming step S104 multiple times or otherwise contacting the treatment composition to the surface of the substrate multiple times.

FIG. 3 shows a substrate where a part of the pattern 40 comprising multiple pattern lines 4 formed on the (patterned) substrate 1 wetted with a solution 5. When a distance between the pattern lines 4 is defined as Space, and when the surface tension of the solution 5 is defined as γ, the power which contributes to the pattern collapse P applied to the pattern 40 is expressed by the following formula:

$$P=2\gamma(\cos \theta)/\text{Space} \quad \text{(Formula 1)}$$

It can be seen from the formula that when θ approaches 90°, cos θ approaches zero and hence the power P of the solution, which is applied to the pattern during the drying step, is reduced. Thereby, it is possible to prevent the pattern from being collapsed during the drying step.

In alternative embodiments, the treatment compositions are applied to the surface of substrates for the purpose of modifying the surface energy between the substrate and another surface that will be brought into contact with the treatment composition on the substrate, which may be used to increase or decrease the adhesiveness between the two surfaces.

(Step S107) This optional step involves removing the hydrophobic film formed on the surface of the (patterned) substrate 1, which may be done by an ashing step, such as dry ashing and/or ozone gas treatments.

When the method of this invention using a treatment composition of this invention is used to form a hydrophobic film on the (patterned) substrate, the pattern collapse that might have otherwise occurred during the drying step can be prevented or reduced. Pattern collapse is typically worse when the pattern height H (shown in FIG. 2) which is measured from the surface of the substrate to the upper surface of the pattern is taller, the pattern line 4 thicknesses t are thinner, and the Space between the pattern lines is smaller. Pattern lines that are taller and thinner are typically said to have a high aspect ratio.

Figure 4:
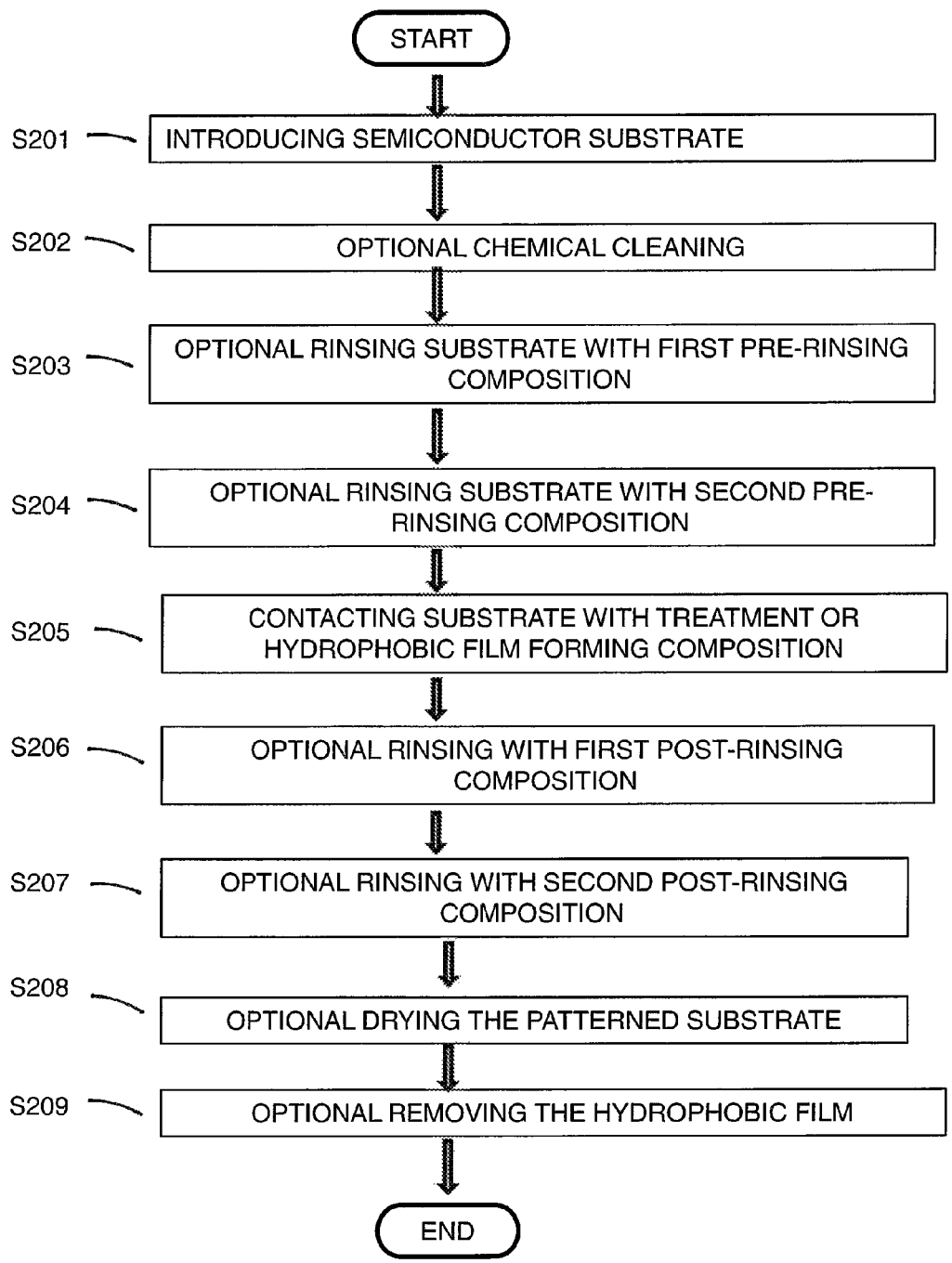
FIG. 4 is a flow chart for explaining a surface treatment method according to a second embodiment of the present invention.
Figure 5:
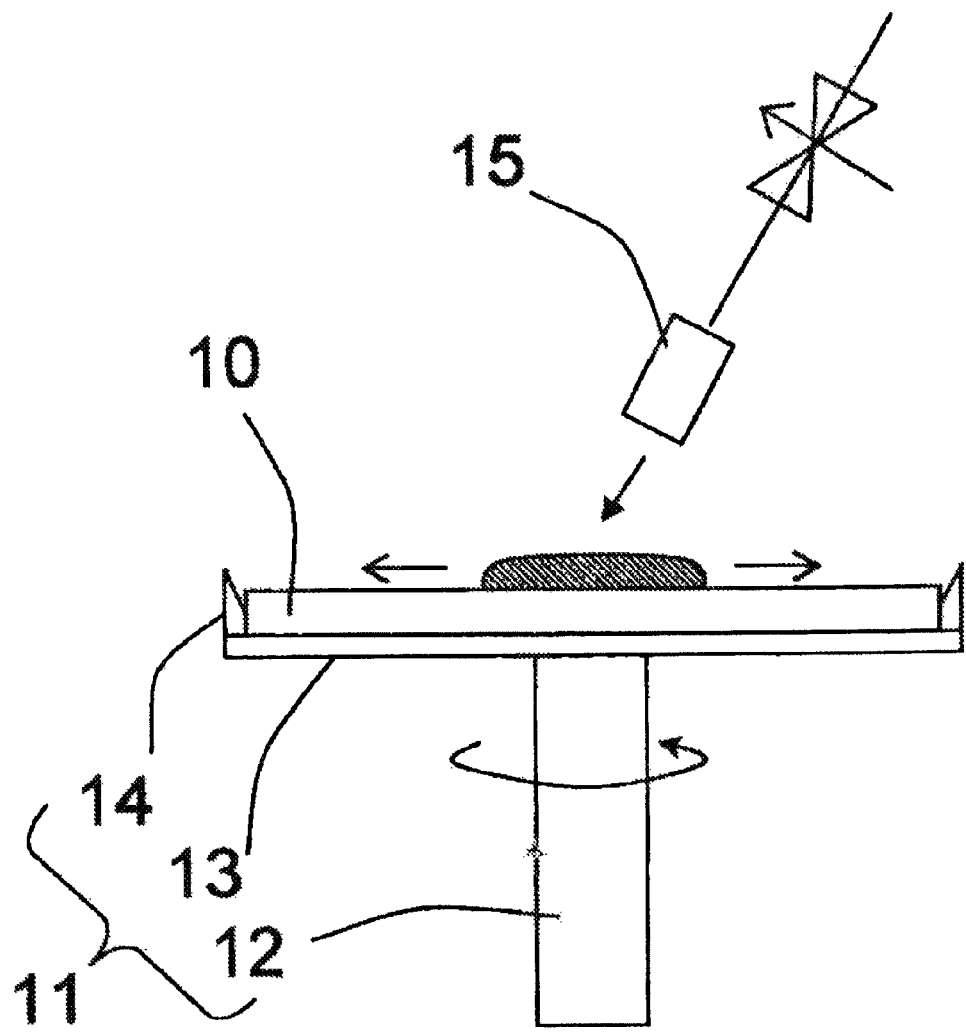
FIG. 5 is a figure showing a schematic configuration of a surface treatment apparatus according to the second embodiment.

An alternative embodiment of a method of treating the surface of a semiconductor substrate, which may be a (patterned) substrate, will be described with reference to a flow chart shown in FIG. 4, and a cross sectional view of the main part of a surface treatment apparatus shown in FIG. 5. The surface treatment apparatus shown in FIG. 5 is a single wafer type which performs treatment of one (patterned) substrate at a time by supplying a treatment composition (which may be a solution) to the (patterned) substrate.

Step S201 involves mounting a (patterned) substrate (wafer) 10 to be treated on a spin chuck. The substrate is delivered by a carrying section (not shown) to a spin chuck 11. The spin chuck 11 is a substrate holding and rotating mechanism by which the (patterned) substrate 10 is substantially horizontally held and rotated.

The spin chuck 11 includes a rotating shaft 12 extended in substantially vertical direction, a disk-like spin base 13 attached to the upper end of the rotating shaft 12, and a chuck pin 14 which is provided at the periphery of the spin base 13 and is configured to hold the substrate.

Step S202 involves an optional step of contacting the (patterned) substrate with a chemical cleaning solution. The (patterned) substrate 10 is rotated at a predetermined rotation speed, and the chemical cleaning solution is supplied near the rotation center of the surface of the (patterned) substrate 10 from a nozzle 15 provided above the spin chuck 11. The chemical cleaning solution may be, for example, a sulfuric acid ($H_2SO_4$) and hydrogen peroxide ($H_2O_2$) mixture (SPM), or hydrofluoric acid solution.

The chemical cleaning solution, if used, is made to spread over the entire surface of the (patterned) substrate 10 by being subjected to the centrifugal force caused by the rotation of the (patterned) substrate 10, and thereby a cleaning step of the (patterned) substrate 10 is performed.

Step S203 involves the optional step of pre-rinsing the substrate in a first optional pre-rinsing step. The first pre-rinsing step, if used, may, for example, comprise or be water. The water or other pre-rinsing composition may be supplied near the rotation center of the surface of the (patterned) substrate 10 from the nozzle 15. The first optional pre-rinsing composition is made to spread over the entire surface of the (patterned) substrate 10 by being subjected to the centrifugal force caused by the rotation of the (patterned) substrate 10. Thereby, a first pre-rinsing, if used, is performed to wash away the optional chemical solution left on the surface of the (patterned) substrate 10 by optional Step 202.

Step S204 involves a second optional pre-rinsing step of the (patterned) substrate. The second pre-rinsing composition, if used, may be or comprise an alcohol, such as IPA. The second pre-rinsing composition may be supplied near the rotation center of the surface of the (patterned) substrate 10 from the nozzle 15. The second pre-rinsing composition is made to spread over the entire surface of the (patterned) substrate 10 by being subjected to the centrifugal force caused by the rotation of the (patterned) substrate 10. Thereby, the second pre-rinsing step substitutes the second pre-rinsing composition for the first pre-rinsing composition if left on the surface of the (patterned) substrate 10 or otherwise may remove the first pre-rinsing composition from the surface of the (patterned) substrate. The second pre-rinse solution, if used, may be an organic solvent that is miscible with both the first pre-rinse solution (which may be water) and the treatment composition (hydrophobic-film-forming composition) applied in the next or following step. In some embodiments, the first pre-rinse step may involve contacting the substrate with water, followed by a second pre-rinse step which involves contacting the substrate with alcohol, for example, IPA, and a third pre-rinsing step which involves contacting the substrate with an organic solvent, for example, glycol ether or a water-immiscible solvent.

Step S205 involves contacting the substrate with a treatment or hydrophobic-film-forming composition of this invention to coat the (entire surface unless the surface has a mask thereon to prevent the treatment composition from contacting the entire) surface of the substrate (wafer). The treatment composition (hydrophobic-film-forming composition) may be supplied near the rotation center of the surface of the (patterned) substrate 10 from the nozzle 15.

The treatment composition (hydrophobic-film-forming composition) is made to spread over the entire surface of the (patterned) substrate 10 by being subjected to the centrifugal force caused by the rotation of the (patterned) substrate 10. Thereby, a hydrophobic film with low wettability and/or having other surface modifying characteristics is formed on the surface of the (patterned) substrate 10. The materials that tend to be modified with organosilane adsorbates may include oxides (silicone dioxide, tetraethyl orthosilicate (TEOS), thermal oxide and low-k materials). The materials that tend to be modified with organophosphonic acid adsorbates may include nitrides (titanium nitride, tantalum nitride, aluminum nitride) as well as certain types of metal surfaces (including copper, silver or gold).

Optional Step S206 involves an optional first post-rinsing of the (patterned) substrate with a first post-rinsing composition. The first optional post-rinsing composition may be an alcohol, such as IPA, or an alcohol solution. To perform the first post-rinsing step, the first post-rinsing composition may be supplied near the rotation center of the surface of the (patterned) substrate 10 from the nozzle 15. The first post-rinsing composition is made to spread over the entire surface of the (patterned) substrate 10 by subjecting it to the centrifugal force caused by the rotation of the (patterned) substrate 10. Thereby, a first post-rinsing step, if performed, may remove the excess of the hydrophobic-film-forming composition left on the surface of the (patterned) substrate 10.

Step S207 involves optional rinsing the (patterned) substrate with a second post-rinsing composition. The second post-rinsing composition, which may be water, may be supplied near the rotation center of the surface of the (patterned) substrate 10 from the nozzle 15. The optional second post-rinsing composition is made to spread over the entire surface of the (patterned) substrate 10 by the centrifugal force on it caused by the rotation of the (patterned) substrate 10. Thereby, a second post-rinsing step, if performed may remove, replace and/or wash away any first post-rinsing composition left on the surface of the (patterned) substrate 10.

Optional Step S208 involves drying the (patterned) substrate 10. In one embodiment of the invention, the (patterned) substrate may be dried by spinning the (patterned) substrate 10 to dry it, which may be referred to as a spin dry step. The rotation speed of the (patterned) substrate 10 may be increased to a predetermined spin dry rotation speed, so as to shake off the first or second or other post-rinsing composition left on the surface of the (patterned) substrate 10.

In an alternative embodiment, the (patterned) substrate 10 may be dried by creating a supercritical state in a chamber in which the (patterned) substrate 10 was previously introduced. In such a state, a first or second or other post-rinsing composition, such as IPA, covering the (patterned) substrate is substituted by a supercritical fluid, and the supercritical fluid is gasified by suitably changing the pressure and temperature inside the chamber. It is possible to use $CO_2$, $N_2$, $H_2$, Ar, HFE, or the like as the supercritical fluid.

As a result of the methods of this invention, the (pattern formed on the patterned) substrate 10 is covered by the hydrophobic film, and hence the contact angle θ of the fluid is made to become large (close to 90°). Thereby, since cos θ approaches zero, the power which contributes to the pattern collapse, which is applied to the pattern during the drying step, is reduced, so that the pattern collapse can be prevented or reduced. In alternative embodiments wherein the semiconductor substrate may or may not comprise a pattern thereon, the treatment composition may modify the surface characteristics of the one or more areas of the surface of the substrate and/or repair damaged areas (for example, low k restoration) of the surface. The treatment composition which may comprise one or more silane-and-phosphorus-containing compounds may covalently bond to one or more materials on the substrate, for example, nitrides and/or oxides present at the surface.

Step S209 involves the optional step of removing the hydrophobic film by using for example an ashing step, such as dry ashing and ozone gas treatments, so that the hydrophobic film formed on the surface of the (patterned) substrate 10 is removed and the dry (patterned) substrate is ready for further processing.

In one embodiment, the optional pre-rinse step (step S204) performed before and the post-rinse step (step S206) performed after the contacting the treatment composition to the surface of the substrate step and forming a coating of the treatment composition (hydrophobic film) on at least some portion of the surface thereon (step S205) may each comprise any type of organic solvent or organic solvent mixture that preferably is miscible with both water and the treatment composition (hydrophobic film forming solution). Those solvent compositions include alcohol (such as IPA), glycol ethers, other water-miscible solvent such as NMP and DMSO. In other embodiments, the treatment or hydrophobic-film-forming compositions used to form the coating of the treatment composition (hydrophobic film) in one or more areas of on the surface of the substrate cannot replace water on the (patterned) substrate, for example, some treatment compositions (hydrophobic-film-forming compositions) of this invention comprise water immiscible solvents. (Water immiscible solvents have a solubility of less than 1 wt % in water.) In those embodiments, it may be desirable to use a multi-step pre-rinse, for example, the first pre-rinse step may involve contacting the substrate with water (DI water of the like), followed by a second pre-rinse step involving contacting the substrate with alcohol, for example, IPA, glycol ethers, such as ethoxy ethanol, butoxy ethanol, ethoxy-2-propanol, propoxy ethanol, butoxy propanol and other glycol ethers, NMP; glycols such as ethylene glycol, propylene glycol, butylenes glycol; and a third pre-rinsing step which involves contacting the substrate with water-immiscible organic solvent which may be a mixture of solvents, for example, silicone oil, $C_{1-40}$ aliphatic hydrocarbons; $C_{1-40}$ aromatic hydrocarbons, substituted naphthalenes, d-limonene, l-limonene, dl-limonene, orange peel oil, dipentene, halogenated hydrocarbons (examples listed earlier herein), fluorinated hydrocarbons (examples listed earlier herein), and mixtures thereof. Mixtures of two or more solvents may also be employed. or any of the organic solvents described herein. In some embodiments the second pre-rinsing step is optional. In other embodiments, the third pre-rinsing step is optional.

For clarity, the terms "pre-rinse step" and "pre-rinse composition" are used to indicate the application of a composition (the pre-rinse composition) to rinse the (patterned) substrate before the application of the treatment or hydrophobic-film-forming composition to the (patterned) substrate. The terms "post-rinse step" and "post-rinse composition" are used to indicate the application of a composition (the post-rinse composition) to rinse the (patterned) substrate after the application of the treatment or hydrophobic-film-forming composition to the (patterned) substrate. If there are more than one pre-rinse steps and more than one pre-rinse compositions, and/or more than one post-rinse steps and more than one post-rinse compositions, the first pre-rinse steps or post-rinse steps occur first in time relative to the second and/or other pre-rinse steps or post-rinse steps.

The pre-rinse compositions of this invention may comprise any of the following: water, alcohols such as IPA. The post-rinse compositions may comprise any of the following: alcohols such as IPA, aqueous alcohol, or water. Additional examples of useful pre-rinse and post-rinse compositions that may be water miscible organic solvent or organic solvent mixtures include glycol ethers such as ethoxy ethanol, butoxy ethanol, ethoxy-2-propanol, propoxy ethanol, butoxy propanol and other glycol ethers; glycols such as ethylene glycol, propylene glycol, butylenes glycol; alcohols such as methanol, ethanol, propanol, iso-propanol, butanol, iso-butanol, amyl alcohol and other aliphatic alcohols. Mixtures of two or more solvents may also be employed. Note in some embodiments, water may not be used either as a pre-rinse and/or post-rinse solution and/or water immiscible solvents may be required.

The pre-rinse and post-rinse compositions may contact the (patterned) substrate (having, for examples, metal, dielectric and/or hardmask layers or no layers thereon) under an atmosphere containing one or more of air, an inert gas, ozone, and oxygen. Inert gases include the noble gases, such as helium, neon, argon, krypton, xenon, and nitrogen.

In alternative embodiments, additional optional rinsing steps can be provided before and/or after contacting the (patterned) substrate with the treatment composition (hydrophobic-film-forming composition) of this invention.

In one particular embodiment an alcohol rinse is used after a water rinse step prior to applying the treatment composition (hydrophobic-film-forming composition) to create the (hydrophobic) film on at least some areas of the surface of the (patterned) substrate and another alcohol rinse step can be used after the treatment composition (hydrophobic-film-forming composition) is coated on at least some areas of the surface of the substrate to remove excess treatment composition (hydrophobic-film-forming composition). In another embodiment, one or more rinsing steps using one or more organic solvents can be added before and/or after the application of the treatment composition (hydrophobic-film-forming composition) to the substrate. In one embodiment the solvent rinsing step follows an alcohol rinsing step. It is known that when water is mixed with certain types of treatment compositions (hydrophobic-film-forming compositions) (for example in step S205), hydrolysis of the treatment or hydrophobic-film-forming composition may be caused so that the water repellent performance of the treatment or hydrophobic-film-forming composition may be deteriorated. The deterioration of the water repellent performance reduces the effect of preventing the pattern collapse or other benefits of applying the treatment composition. It is in those embodiments that the solvent rinse may be added to the method of this invention after the alcohol rinse step. In some embodiments a water rinse step may precede the alcohol rinse step. Thus, in one embodiment, after the water rinse there will be an alcohol rinse to remove the water after which there may be an optional solvent rinse step and then the (patterned) substrate may be coated with the treatment or hydrophobic-film-forming composition.

The hydrophobic film may be formed or partially formed by the occurrence of condensation reaction between hydroxyl groups on the substrate and leaving groups (halogen, alkoxy groups, etc.). When present on a patterned substrate it helps to prevent pattern collapse.

Although the embodiments have been described with reference to batch type surface treatment apparatus, or single wafer type surface treatment apparatus, it is possible to use the steps described in either embodiment with a batch-type surface treatment apparatus and for a single wafer-type surface treatment apparatus.

In the above described embodiments, the ashing step for removing the hydrophobic film may be performed after the drying step of the (patterned) substrate. However, in the case where an RIE (reactive ion etch) process is performed after the drying step, the ashing step need not be performed because the hydrophobic film is also removed in the RIE process.

As described above, in the surface treatment method according to the embodiments of the invention, pattern collapse can be prevented by applying the treatment composition thereto so that the force applied to the pattern during the drying step is made very small by controlling the wettability represented by a value of cos θ.

In alternative embodiment of this invention, the treatment composition can be used to restore a low k film that were damaged by plasma etching process during the pattern forming. The surface damaged by plasma treatment has lost some degree of hydrocarbon moiety of the original film structure, as well as number of hydrophilic functional groups (such as —OH) were formed. The treatment composition may readily react with those hydrophilic groups, depositing hydrocarbon moiety as an alkyl groups attached to organosilane component, making surface more hydrophobic and restoring hydrocarbon moiety on the surface.

In another alternative embodiment of this invention, the treatment composition can be used to modify the surface of a semiconductor or MEMS substrate by the method of applying the treatment composition to the surface of a semiconductor substrate. The treatment composition can be used to increase or decrease the surface energy, in one embodiment, the treatment composition may cause two surfaces to adhere to one another. The treatment composition can be applied using a mask to provide protection to portions of the surface of a semiconductor or MEMS substrate.

Example 1

Figure 6:
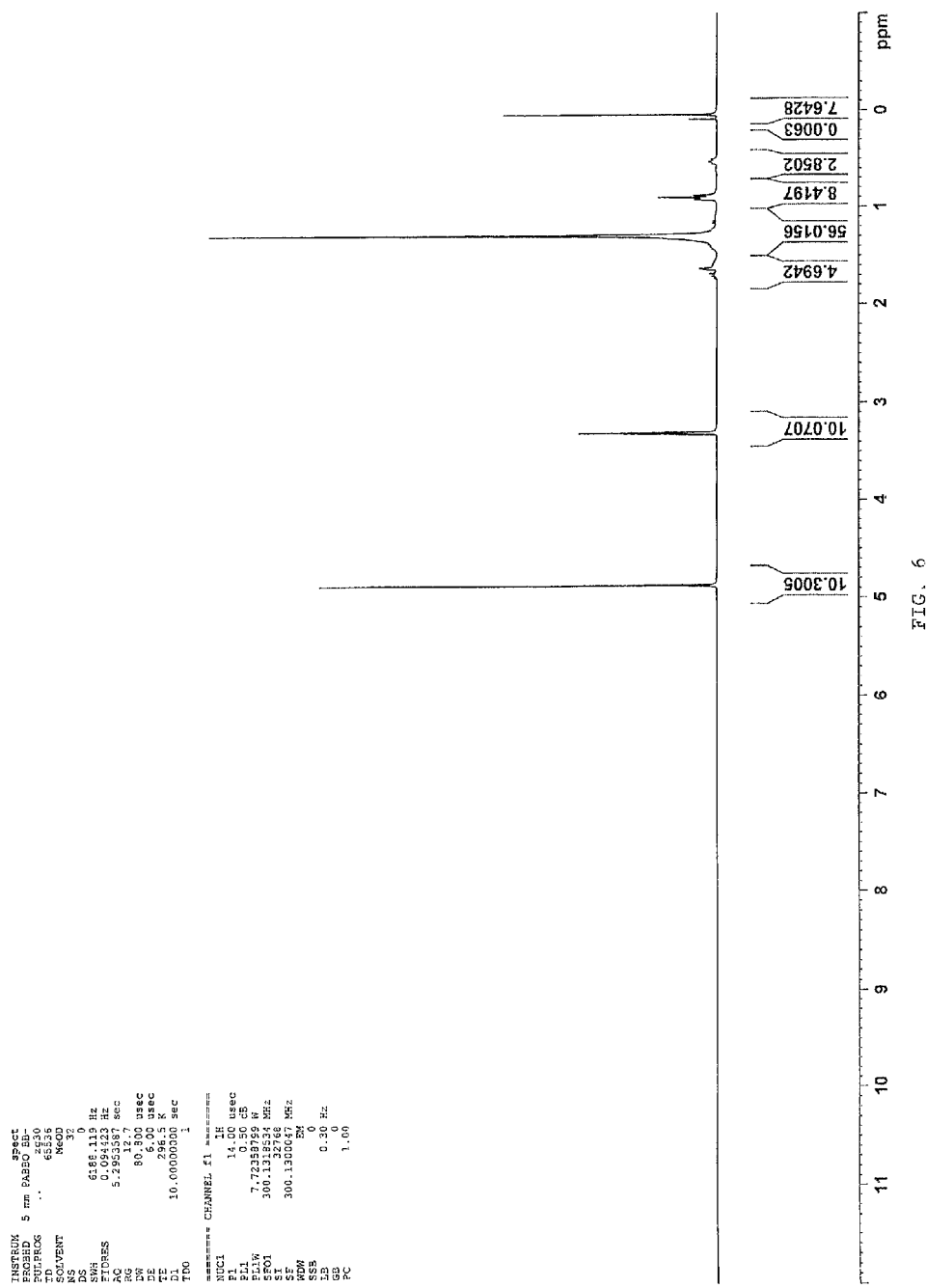
FIG. 6 is a nuclear magnetic resonance (NMR) of a component of one embodiment of the treatment composition of this invention.

The following is a description of the formation of a treatment composition of this invention:

Synthesis of dimethyloctylsilyl octadecylphosphonate. In a 50 mL glass vial, 1.96 g of chlorodimethyloctylsilane and 3.20 g of octadecylphosphonic acid (ODPA) were mixed, with the vial's cap loosely closed. The vial was placed in a bath of silicone oil for heating, and the oil bath temperature was raised to 90° C. for 4 h. The solid dissolved into the liquid when the temperature was elevated, and the oil bath temperature was kept at 90° for 4 hours. The mixture was then cooled down, dissolved into IPA and filtered (the operation to remove unreacted ODPA if any). Colorless solid was recrystallized from the solution by IPA evaporation, and the solid was subject to NMR analysis (300 MHz Bruker NMR). $^1$H NMR (CD$_3$OD) δ: 0.0 (s, 6H, Si(CH$_3$)$_2$, 0.55 (t, J=7 Hz, 2H, C1 CH$_2$), 0.92 (t, J=7 Hz, 6H, C8 and C18' CH$_2$), 1.2-1.5 (m, 42H, C2~C7 and C3'~H17' CH$_2$), 1.5-1.8 (m, 4H, C1' and C2' CH$_2$). The NMR is shown in FIG. 6. The structure below indicates the peak assignments to the structure:

Example 2

Treatment or hydrophobic-film-forming compositions were made by combining components in the amounts indicated in the following tables by mixing the components at room temperature. The change in hydrophobicity of the substrates of interest by hydrophobic-film-forming compositions of present invention were tested using the following blanket substrates:
Damaged Low-k film (Air Products DEMS C8 or DEMS ATRP) damaged by O$_3$ plasma 4 minutes
TEOS (purchased from Silicon Valley Microelectronics (SVM): 7000 Å thickness, undoped undensified)

The TEOS film substrate was pre-treated with dilute HF (1:500) for 60 seconds, followed by DI water rinse and nitrogen spray dry. This step is employed to remove any alteration of surface caused by atmospheric oxygen or other species in storage atmosphere of substrates. (The damaged low-k substrate was not pretreated.)

Static contact angle (c/a) with DI water were measured with goniometer system (by Rame-Hart, Succasunna, N.J.). 3 measurements were taken on the surface of each piece and the arithmetic mean of the measurements is reported.

After measuring the contact angle on an untreated substrate at Time equal to 0 second, the substrate processing with the treatment or hydrophobic-film-forming compositions were performed by directly immersing numerous substrates into each treatment or hydrophobic-film-forming compositions for a period of time. At each time interval one substrate was taken out of the treatment composition, rinsed with isopropanol, then underwent a nitrogen spray dry and the contact angle was measured for each.

Raw data of goniometer reading follows in the Table I below for the treatment compositions in Table II. The treatment compositions in Table II were made by adding the amounts of the components listed for each of the Examples in Table II (which are in grams) into a 150 ml glass beaker at room temperature with stirring for 20 hours.

The tests described above used to generate the data in Tables I and II were repeated, except that a Titanium nitride film on a blank substrate was used without pretreatment. The TiN film substrates were from SVM. The change in contact angle for the TiN film and the treatment compositions tested are in Tables III and IV.

TABLE I

| Examples | Time (sec) | damaged low-k film Average | TEOS film Average |
| --- | --- | --- | --- |
| 115L | 0 | 7.85 | 6.27 |
|  | 10 | 86.89 | 80.30 |
|  | 19 | 84.02 | 80.45 |
|  | 35 | 88.87 | 86.98 |
|  | 64 | 88.08 | 84.77 |
|  | 120 | 91.64 | 88.38 |

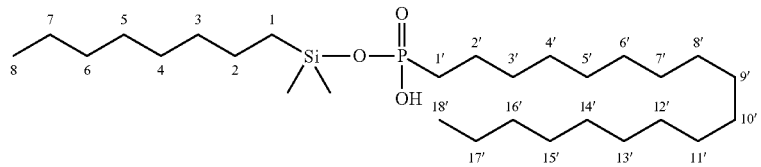 [SMILES: CCCCCCCCCCCCCCCCCCP(=O)(O)O[Si](C)(C)CCCCCCCC]

TABLE I-continued

| Examples | Time (sec) | damaged low-k film Average | TEOS film Average |
|---|---|---|---|
| 115N | 0 | 7.85 | 6.27 |
|  | 10 | 81.40 | 81.63 |
|  | 19 | 84.88 | 83.50 |
|  | 35 | 91.30 | 88.92 |
|  | 64 | 94.88 | 88.75 |
|  | 120 | 90.93 | 88.98 |
| 115O | 0 | 7.85 | 6.27 |
|  | 10 | 81.40 | 82.03 |
|  | 19 | 83.28 | 84.78 |
|  | 35 | 86.03 | 85.20 |
|  | 64 | 86.98 | 88.08 |
|  | 120 | 88.92 | 87.63 |
| 115P | 0 | 7.85 | 6.27 |
|  | 10 | 82.32 | 80.72 |
|  | 19 | 84.55 | 80.28 |
|  | 35 | 86.57 | 82.70 |
|  | 64 | 87.13 | 84.07 |
|  | 120 | 89.35 | 84.77 |
| 95X1 | 0 | 7.85 | 6.27 |
|  | 10 | 33.58 | 39.25 |
|  | 19 | 40.32 | 42.05 |
|  | 35 | 45.47 | 48.35 |
|  | 64 | 47.78 | 52.95 |
|  | 120 | 54.62 | 58.27 |

TABLE II

| | Examples | | | | |
|---|---|---|---|---|---|
| Components | 115L | 115N | 115O | 115P | 95X1 |
| PDMS (GE SF96-5 Silicone) | 5.00 | 5.00 | 5.00 | | |
| chlorotrimethlylsilane | | | 94.90 | 96.90 | |
| chlorodimethyloctylsilane | 74.90 | 94.90 | | 3.00 | 2.50 |
| d-Limonene | 20.00 | | | | 97.49 |
| Octadecylphosphonic acid | 0.10 | 0.10 | 0.10 | 0.10 | 0.01 |

TABLE III

| | Examples TiN film | | |
|---|---|---|---|
| Time [sec] | Comparative Example | 126C | 126B |
| 0 | 57.9 | 57.9 | 57.9 |
| 10 | 57.1 | 79.6 | 73.4 |
| 60 | 66.2 | 82.4 | 81.3 |
| 120 | 77.4 | 84.4 | 81.8 |

TABLE IV

| | Examples | | | | |
|---|---|---|---|---|---|
| Components (in grams) | Comparative Example | 126C | 126B | 95Y | 95Z |
| Chlorodimethyloctyl silane | 100.0 | 97.5 | 97.4 | 3.00 | 3.00 |
| GE SF96-5 Silicone | 0.0 | 2.5 | 2.5 | 0.0 | 0.0 |
| Octadecylphosphonic acid | 0.0 | 0.1 | 0.1 | Saturated | 0.03 |
| 1-octanol | 0.0 | 0.0 | 0.0 | 97.0 | 96.97 |

Comparative Examples

Comparative Examples in Tables V and VI show attempts to dissolve octadecylphosphonic acid into NMP. A 150 ml beaker was used. The components were added to the beaker with stirring at the temperatures indicated in the table. The appearance of the mixture in the beaker was recorded after 20 hours of stirring. The maximum amount of octadecylphosphonic acid dissolved into NMP at room temperature was 0.18 grams, into 99.98 grams of NMP.

TABLE V

| Components | Comparative Examples | | | | | |
|---|---|---|---|---|---|---|
| (grams) | 74A | 74B | 74C | 74D | 74E | 74F |
| N-methyl-pyrrolidinone | 99.84 | 99.89 | 99.87 | 99.85 | 99.89 | 99.90 |
| Octadecyl-phosphonic acid | 0.163 | 0.114 | 0.130 | 0.146 | 0.110 | 0.099 |
| Mixture appearance (@ 25° C.) | Not clear | Not clear | Not clear | Not clear | Not clear | Not clear |

TABLE VI

| Components | Comparative Examples | | | | | |
|---|---|---|---|---|---|---|
| (grams) | 74G | 74H | 74I | 74J | 74K | 74L |
| N-methyl-pyrrolidinone | 99.91 | 99.93 | 99.94 | 99.95 | 99.97 | 99.98 |
| Octadecyl-phosphonic acid | 0.088 | 0.070 | 0.060 | 0.048 | 0.030 | 0.018 |
| Mixture appearance (@ 25° C.) | Not clear | Not clear | Not clear | Not clear | Not clear | Clear |

Example 3

Examples in Tables VII and VIIII show solutions of octadecylphosphonic acid in solvents comprising 1-octanol. A 150 ml beaker was used. The components were added to the beaker with stirring at the temperatures indicated in the table. The appearance of the mixture in the beaker was recorded after 20 hours of stirring. A clear solution indicates that the solvent dissolved the octadecylphosphonic acid. The results recorded for the Examples in Tables VII and VIII show that 1-octanol is a good solvent relative to NMP for octadecylphosphonic acid. Octanol can be used in solvent mixtures with other known solvents to dissolve higher amounts octadecylphosphonic acid in solution as compared to NMP alone. The solvents that can be used in combination with the octanol are not limited and include any of the organic solvents listed above and include glycol ether, propylene glycol and NMP.

By comparing Example 74L to Examples of the invention 115L-P and 126B, 126C, 95Y and 95X, it can be seen that after reacting the silane-containing component and the phosphorus-containing component to form a silane-and-phosphorus-containing-reaction product (silane-and-phosphorus-containing compound), the silane-and-phosphorus-containing-reaction product increases the solubility of the phosphorus-containing component in organic solvents and other solvents to form the treatment compositions of this invention. The comparative examples provided dissolution of about 0.01% by weight of the total composition at room temperature in only certain limited solvents, e.g. NMP. In contrast, the silane-and-phosphorus-containing-reaction product is easily dissolved at room temperature (24° C.) in amounts greater than 0.01%, or greater than 0.02%, or greater than 0.03%, or greater than 0.05%, or greater than 0.07%, or greater than 0.1%, or greater than 0.2% or greater than 0.5% by weight or from 0.01 to 25% by weight in many known solvents (or from 20% or 70% by weight or from 20% or 60% by weight) increasing its usefulness in a treatment composition to coat at least some areas of the surface of a semiconductor or MEMS substrate.

TABLE VII

| Components(grams)/ | Examples | | | | |
|---|---|---|---|---|---|
| Results | 96K | 96L | 96M | 96N | 96O |
| Octadecylphosphonic acid | 0.163 | 0.326 | 0.033 | 0.065 | 0.033 |
| Glycol ether PM (DPM) | | | 80.00 | 80.00 | |
| Propylene glycol | | | | | 80.00 |
| 1-Octanol | 100.00 | 100.00 | 20.00 | 20.00 | 20.00 |
| N-Methylpyrrolidinone | | | | | |
| Mixture appearance (@ 25° C.) | Clear | Clear | Clear | Clear | Clear |
| Mixture appearance (@ 4° C.) | Clear | Little turbidity | Clear | Clear | Clear |
| Mixture appearance (@ −18° C.) | Solvent frozen | Solvent frozen | Clear | Not clear | Clear |

TABLE VIII

| | Examples | | | |
|---|---|---|---|---|
| Components(grams)/Results | 96P | 96Q | 96R | 96S |
| Octadecylphosphonic acid | 0.065 | 0.033 | 0.065 | 0.065 |
| Glycol ether PM (DPM) | | | | 40.00 |
| Propylene glycol | 80.00 | | | 40.00 |
| 1-Octanol | 20.00 | 20.00 | 20.00 | 20.00 |
| N-Methylpyrrolidinone | | 80.00 | 80.00 | |
| Mixture appearance (@ 25° C.) | Clear | Clear | Clear | Clear |
| Mixture appearance (@ 4° C.) | Clear | Clear | Clear | Clear |
| Mixture appearance (@ −18° C.) | Not clear | little turbidity | Not clear | Clear |

This invention has been described with reference to particular embodiments, it is understood that variations known to a person of ordinary skill in the art can be made to those embodiments and still be within the scope of the invention as claimed.

The invention claimed is:

1. A treatment composition comprising a silane-and-phosphorus-containing compound formed by reacting a mixture comprising one or more silane-containing components and one or more phosphorus-containing components wherein at least one of the silane-containing components has the following structure:

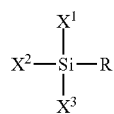

where R is selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups or halogen-substituted heteroaryl groups, ether, amine, ester, amide, and alkoxy groups, with the proviso that there is no hydrogen bonded to a nitrogen or an oxygen in said silane-containing component of structure (0);

$X^1$, $X^2$ and $X^3$ are independently selected from the group consisting of halogens, alkoxy groups, organic acid groups, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester and amide groups, with the proviso that at least one of $X^1$, $X^2$ and $X^3$ is selected from the group consisting of a halogen, an alkoxy group or an organic acid group;

and at least one of said one or more phosphorus-containing components has the following structure:

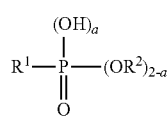

where, a is 1 or 2, and $R^1$ and $R^2$ are independently selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester, amide, and alkoxy groups;

and optionally further comprising one or more non-aqueous solvents.

2. The treatment composition of claim 1 further wherein at least one of said $X^1$, $X^2$, or $X^3$ is a halogen.

3. The treatment composition of claim 1 further wherein one, and only one, of said $X^1$, $X^2$, or $X^3$ is a halogen.

4. The treatment composition of claim 1 further wherein $X^1$ is a halogen and $X^2$, $X^3$, and R are independently selected from unsubstituted alkyl, aryl, and heteroaryl groups or fluorine-substituted alkyl, aryl, and heteroaryl groups.

5. The treatment composition of claim 1 wherein said silane-containing component of structure (0) is selected from the group consisting of alkoxydimethylalkylsilane, dialkoxymethylalkylsilane, trialkoxyalkylsilane, chlorodimethylalkylsilane, dichloromethylalkylsilane, trichloroalkylsilane, alkoxydiethylalkylsilane, dialkoxyethylalkylsilane, trialkoxyalkylsilane, chlorodiethylalkylsilane, dichloroethylalkylsilane, in which the alkyl groups independently comprise 1 to 30 carbons, and wherein said carbons may have halogens substituted for some or all hydrogens attached to said carbons, and the alkoxy groups may be any $C_1$-$C_8$ alkoxy group, and may comprise halogens substituted for some or all hydrogens in the alkoxy groups.

6. The treatment composition of claim 1 wherein said R comprises 7 to 30 carbons.

7. The treatment composition of claim 1 wherein said a is 2, and said $R^1$ comprises 4 to 30 carbon atoms in any of the substituted and unsubstituted alkyl, aryl and heteroaryl groups.

8. The treatment composition of claim 1 wherein said phosphorus-containing component of structure (4) is selected from the group consisting of octadecylphosphonic acid, octylphosponic acid, decylphosponic acid, dodecylphosponic acid, tetradecylphosponic acid, hexadecylphosponic acid, eicosylphosponic acid, docosylphosphonic acid and tetracosylphosphonic acid.

9. The treatment composition of claim 1 comprising said one or more silane-containing components of structure (0) in excess of an amount that will react with said one or more phosphorus-containing component of structure (4).

10. The treatment composition of claim 1 further comprising said one or more non-aqueous solvents selected from the group consisting of: silicone oil, 3,3',4,4'-oxydiphthalic dianhydride, benzyl alcohol, 1-octanol, NMP, glycol ether, $C_{1-40}$ aliphatic hydrocarbons; $C_{1-40}$ aromatic hydrocarbons; substituted naphthalenes, d-limonene, l-limonene, dl-limonene, orange peel oil, dipentene, halogenated hydrocarbons, fluorinated hydrocarbons, silane-containing components of structure (0), and mixtures thereof.

11. The treatment composition of claim 1 further comprising one or more non-aqueous solvents selected from the group consisting of: silane-containing components of structure (0), silicone oil, hexane, octane, decane, dodecane, tetradecane, hexadecane, octadecane, icosane, benzene, toluene, xylene, mesitylene, naphthalene, methylnaphthalene, dimethylnapthalene, trimethylnapthalene, tetramethylnapthalene, tetrahydronaphthalene, d-limonene, l-limonene, dl-limonene, orange peel oil, dipentene, methylene chloride, chloroform, 1,1,1-trichloroethane, trichloroethylene; fluorochlorohydrocarbons, fluorochlorocarbons, chlorohydrocarbons, fluorohydrocarbons, fluorocarbons, chlorocarbons, ethers of fluorochlorohydrocarbon with hydrocarbon, fluorochlorohydrocarbons, fluorochlorocarbons, chlorohydrocarbons, fluorohydrocarbons, fluorocarbons or chlorocarbons; ethers of fluorochlorocarbon with hydrocarbon, fluorochlorohydrocarbons, fluorochlorocarbons, chlorohydrocarbons, fluorohydrocarbons, fluorocarbons or chlorocarbons; ethers of chlorohydrocarbon with hydrocarbon, fluorochlorohydrocarbon, fluorochlorocarbon, chlorohydrocarbon, fluorohydrocarbon, fluorocarbon or chlorocarbons; ethers of fluorohydrocarbon with hydrocarbon, fluorochlorohydrocarbons, fluorochlorocarbons, chlorohydrocarbons, fluorohydrocarbons, fluorocarbons or chlorocarbons; ethers of fluorocarbon with hydrocarbon, fluorochlorohydrocarbon, fluorochlorocarbon, chlorohydrocarbon, fluorohydrocarbon, fluorocarbon or chlorocarbon; ethers of chlorocarbon with hydrocarbon, fluorochlorohydrocarbon, fluorochlorocarbon, chlorohydrocarbon, fluorohydrocarbon, fluorocarbon or chlorocarbon; and mixtures thereof.

12. The treatment composition of claim 1 wherein said one or more silane-containing components of structure (0) is selected from the group consisting of chlorotrimethylsilane, chlorodimethyloctylsilane, trichlorooctylamine, bis(triethoxysilyl)ethane, and (tridecafluoro-1,1,2,2-tetrahydrooctyl)trichlorosilane.

13. The treatment composition of claim 1 wherein said treatment composition comprises: (i) 0.01 to 99.999 wt % of the one or more silane-containing components of structure (0); (ii) 0.001 to 60 wt % of the one or more phosphorus-containing components of structure (4); and (iii) 0 to 99.989 wt % non-aqueous solvent (excluding the silane-containing components of structure (0) which are included in (i)) based on the total weight of the composition.

14. The treatment composition of claim 1 wherein said treatment composition comprises: (i) 40 to 99.999 wt % of the one or more silane-containing components of structure (0); (ii) 0.001 to 10 wt % of the one or more phosphorus-containing components of structure (4); and (iii) 0 to 50 wt % non-aqueous solvent (excluding the silane-containing components of structure (0) which are included in (i)) based on the total weight of the composition.

15. The treatment composition of claim 1 wherein said treatment composition comprises: (i) 0.01 to 49.999 wt % of the one or more silane-containing components of structure (0); and (ii) 0.001 to 10 wt % of the one or more phosphorus-containing components of structure (4); and (iii) 50 to 99.989 wt % non-aqueous solvent (excluding the silane-containing components of structure (0) which are included in (i)) based on the total weight of the composition.

16. The treatment composition of claim 1 wherein said silane-and-phosphorus-containing compound is selected from the group consisting of alkylsilyl alkylphosphonates, arylsilyl alkylphosphonates, alkylsilyl arylphosphonates, arylsilyl arylphosphonates, heteroarylsilyl alkylphosphonates, alkylsilyl heteroarylphosphonates, heteroarylsilyl heteroarylphosphonates, aryllsilyl heteroarylphosphonates and heteroarylsilyl arylphosphonates.

17. The treatment composition of claim 1 wherein said silane-and-phosphorus-containing compound comprises dimethylsilyl octadecylphosphonate.

18. The composition of claim 1 said silane-and-phosphorus-containing compound comprises the following structure:

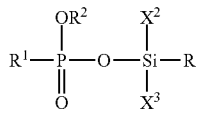

where R is selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester, amide, and alkoxy groups; $X^2$ and $X^3$ are independently selected from the group consisting of halogen, alkoxy groups, organic acid groups, hydrogens, or unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups, halogen-substituted heteroaryl groups, ether, amine, ester and amide groups, with the proviso that there is no hydrogen bonded to a nitrogen or an oxygen in said $X^2$, $X^3$ and R; and $R^1$ and $R^2$ are independently selected from hydrogen, unsubstituted straight, cyclic and branched alkyl groups, unsubstituted aryl groups, unsubstituted heteroaryl groups, substituted straight, cyclic and branched alkyl groups, substituted aryl groups or substituted heteroaryl groups, wherein said substituted alkyl, aryl and heteroaryl groups are selected from halogen-substituted straight, cyclic and branched alkyl, halogen-substituted aryl groups or halogen-substituted heteroaryl groups, ether, amine, ester, amide, and alkoxy groups.

19. The treatment composition of claim 1 further comprising at least one silane-containing component selected from the following structure:

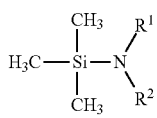
(1)

where $R^1$ represents a hydrogen atom, or a saturated or unsaturated alkyl group; $R^2$ represents a saturated or unsaturated alkyl group, a saturated or unsaturated cycloalkyl group, or a saturated or unsaturated heterocycloalkyl group; and $R^1$ and $R^2$ may link to each other to form a saturated or unsaturated heterocycloalkyl group having a nitrogen atom or the following structure:

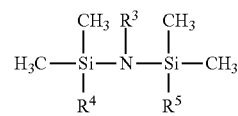
(2)

where $R^3$ represents a hydrogen atom, a methyl group, a trimethylsilyl group, or a dimethylsilyl group; and $R^4$ and $R^5$ each independently represent a hydrogen atom, a methyl group, an alkyl group, or a vinyl group.

20. A treatment composition comprising ocatanol and octadecylphosphonic acid.

21. A substrate comprising the treatment composition of claim 1.

22. A method of treating the surface of a substrate comprising the step of: contacting at least a portion of the surface of a substrate with a treatment composition of claim 1.

23. The method of claim 22 further comprising one or more optional additional steps selected from the steps of: cleaning said substrate; pre-rinsing said substrate in said one or more pre-rinsing steps with one or more optional pre-rinsing compositions prior to said contacting step; post-rinsing said substrate in one or more optional post-rinsing steps with one or more optional post-rinsing compositions; and drying said substrate.

* * * * *